United States Patent
Gewehr et al.

(10) Patent No.: US 6,537,989 B1
(45) Date of Patent: Mar. 25, 2003

(54) AZADIOXACYCLOALKENE DERIVATIVES, METHODS FOR THE PRODUCTION THEREOF AND THEIR USE AS FUNGICIDES AND PEST CONTROL AGENTS

(75) Inventors: Markus Gewehr, Kastellaun (DE); Wassilios Grammenos, Ludwigshafen (DE); Hubert Sauter, Mannheim (DE); Herbert Bayer, Mannheim (DE); Andreas Gypser, Mannheim (DE); Bernd Müller, Frankenthal (DE); Arne Ptock, Ludwigshafen (DE); Oliver Cullmann, Mannheim (DE); Thomas Grote, Schifferstadt (DE); Eberhard Ammermann, Heppenheim (DE); Gisela Lorenz, Neustadt (DE); Siegfried Strathmann, Limburgerhof (DE); Volker Harries, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/806,608
(22) PCT Filed: Oct. 1, 1999
(86) PCT No.: PCT/EP99/07307
§ 371 (c)(1), (2), (4) Date: Apr. 2, 2001
(87) PCT Pub. No.: WO00/21942
PCT Pub. Date: Apr. 20, 2000

(30) Foreign Application Priority Data

Oct. 15, 1998 (DE) .......................... 198 47 592

(51) Int. Cl.⁷ ...................... A61K 31/55; A61K 31/535; A61K 31/41; C07D 267/02; C07D 273/00
(52) U.S. Cl. ............... 514/229.2; 514/211.01; 514/360; 540/544; 544/65; 548/124
(58) Field of Search .......... 514/211.01, 229.2, 514/360; 540/544; 544/65; 548/124

(56) References Cited

U.S. PATENT DOCUMENTS 5,679,676 A    10/1997  Krüger et al. .............. 514/229

FOREIGN PATENT DOCUMENTS

| WO | WO 95/04728 | 2/1995 |
| WO | WO 95/21153 | 8/1995 |
| WO | WO 95/21154 | 8/1995 |
| WO | WO 97/00866 | 1/1997 |
| WO | WO 97/15552 | 1/1997 |
| WO | WO 98/38857 | 9/1998 |

*Primary Examiner*—Brenda Coleman
(74) *Attorney, Agent, or Firm*—Keil & Weinkauf

(57) ABSTRACT

The present invention relates to azadioxacycloalkenes of the formula I

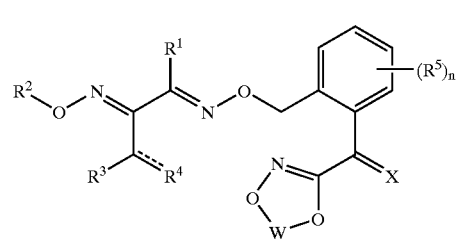

in which the substituents $R^1$ to $R^5$ and X, the index n and the bridge member W have the following meanings:

$R^1$ is $C_1$–$C_4$-alkyl, halogen, $C_1$–$C_4$-haloalkyl, $C_3$–$C_6$-cycloalkyl;

$R^2$ is $C_1$–$C_4$-alkyl, $C_1$–$C_4$-haloalkyl, $C_3$–$C_4$-alkenyl, $C_3$–$C_4$-haloalkenyl, $C_3$–$C_4$-alkynyl or $C_3$–$C_4$-haloalkynyl;

$R^3$ is hydrogen, $C_1$–$C_4$-alkyl, $C_1$–$C_4$-haloalkyl or unsubstituted or substituted phenyl;

$R^4$ is $=CR^aR^b$, —$CR^d=CR^aR^b$ or $=N$—$OR^c$, where $R^a$, $R^b$, $R^c$ and $R^d$ are each as defined in claim 1;

$R^5$ is nitro, cyano, halogen, $C_1$–$C_6$-alkyl or, in the case that n is 2, additionally a bridge which is attached to two adjacent ring atoms;

n is 0, 1, 2, 3 or 4, where the substituents $R^1$ may be different if n is greater than 1;

X is $C_1$–$C_4$-alkoxy-N=, $C_1$–$C_4$-alkoxy-CH= or $R^6$—CH=, where $R^6$ is as defined in claim 1

W is unsubstituted or substituted $C_1$–$C_3$-alkylene.

9 Claims, No Drawings

AZADIOXACYCLOALKENE DERIVATIVES, METHODS FOR THE PRODUCTION THEREOF AND THEIR USE AS FUNGICIDES AND PEST CONTROL AGENTS

This application is a national stage entry under 35 U.S.C. §371 of PCT/EP99/07307 filed Oct. 1, 1999.

The present invention relates to azadioxacycloalkenes of the formula I

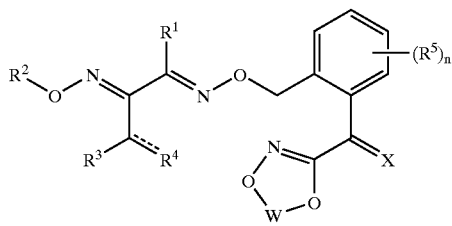

in which the substituents $R^1$ to $R^5$ and A, the index n and the bridge member W have the following meanings:

$R^1$ is $C_1$–$C_4$-alkyl, halogen, cyano, $C_1$–$C_4$-haloalkyl, $C_3$–$C_6$-cycloalkyl;

$R^2$ is $C_1$–$C_4$-alkyl, $C_1$–$C_4$-haloalkyl, $C_3$–$C_4$-alkenyl, $C_3$–$C_4$-haloalkenyl, $C_3$–$C_4$-alkynyl or $C_3$–$C_4$-haloalkynyl;

$R^3$ is hydrogen, $C_1$–$C_4$-alkyl, $C_1$–$C_4$-haloalkyl or unsubstituted or substituted phenyl;

$R^4$ is $=CR^aR^b$, $-CR^d=CR^aR^b$ or $=N-OR^c$, where
  $R^a$, $R^b$, $R^d$ independently of one another are each hydrogen, halogen, $C_1$–$C_6$-alkyl, $C_1$–$C_4$-haloalkyl or unsubstituted or substituted phenyl and
  $R^c$ is one of the radicals mentioned under $R^2$;

$R^5$ is nitro, cyano, halogen, $C_1$–$C_6$-alkyl or in the case that n is greater than 1, is additionally a bridge which is attached to two adjacent ring atoms and which contains three or four members selected from the group: 3 or 4 carbon atoms, 2 or 3 carbon atoms and 1 or 2 nitrogen atoms, oxygen atoms and/or sulfur atoms, where this bridge, together with the ring to which it is attached, may form a partially unsaturated or aromatic radical and where furthermore the carbon atoms of the bridge may be partly or fully substituted by halogen atoms or methyl groups.

n is 0, 1, 2, 3 or 4, where the substituents $R^5$ may be different if n is greater than 1;

X is $C_1$–$C_4$-alkoxy-N=, $C_1$–$C_4$-alkoxy-CH= or $R^6$–CH=, where $R^6$ is halogen, $C_1$–$C_4$-alkyl, $C_1$–$C_4$-alkylthio, $C_1$–$C_4$-alkylamino or di-$C_1$–$C_4$-alkylamino and W is $C_1$–$C_3$-alkylene which is unsubstituted or mono- or disubstituted by $R^7$, where $R^7$ is halogen, cyano, $C_1$–$C_4$-alkyl, $C_1$–$C_4$-haloalkyl, $C_2$–$C_4$-alkenyl, $C_2$–$C_4$-haloalkenyl, $C_2$–$C_4$-alkynyl or $C_2$–$C_4$-haloalkynyl, $C_1$–$C_4$-alkoxy, $C_1$–$C_4$-haloalkoxy, $C_2$–$C_4$-alkenoxy, $C_2$–$C_4$-haloalkenoxy, $C_2$–$C_4$-alkynoxy or $C_2$–$C_4$-haloalkynoxy, $C_1$–$C_4$-alkylcarbonyloxy.

Furthermore, the invention relates to processes for preparing the compounds I, and to compositions and to the use of the compounds I for controlling harmful fungi and animal pests.

Azadioxacycloalkenes having a (Het)aryloxy group in the ortho position are disclosed in the documents WO 95/04728 and WO 97/27189.

α-phenylacrylic acid derivatives and α-phenyl-α-methoximino acetic acid derivatives having a bisoxime ether grouping in the ortho position are described in WO 95/21153, WO 95/18789, and those having a trisoxime ether grouping are described in WO 97/15552.

WO 97/00866, finally, discloses azadioxacycloalkenes having an α-bisoxime ether grouping in the ortho position. In contrast to the compounds known from WO 97/00866, the azadioxacycloalkenes of the invention have an alkenyl or an alkoxyiminoalkyl substituent at the terminal oxime carbon atom of the α-bisoxime ether grouping.

The compounds described in the abovementioned publications are suitable for use as crop protection agents against harmful fungi and in some cases against animal pests.

However, in many instances their activity is unsatisfactory.

It is an object of the present invention to provide compounds having improved activity.

We have found that this object is achieved by the azadioxacycloalkenes of the formula I mentioned at the outset. Furthermore, we have found processes for preparing the compounds I, and the use of the compounds I and of compositions comprising them for controlling harmful fungi and animal pests. Preference is given to the fungicidal activity.

The compounds I can be obtained in a variety of ways, and it is immaterial for the synthesis whether a) the azadioxacycloalkene ring (see Scheme 1) or b) the α-bisoxime ether grouping in the ortho position is synthesized first.

Scheme 1:

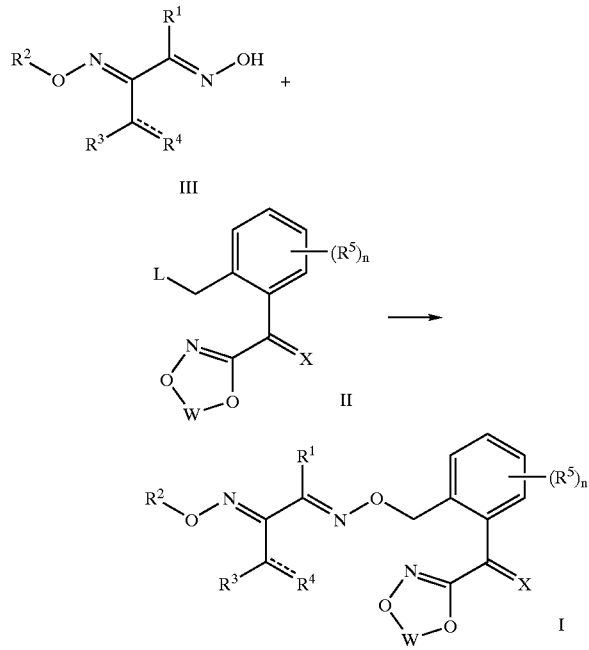

a) Compounds of the formula I are obtained, in particular, by reacting a benzyl compound of the formula II in which the radicals $R^5$, X and W are each as defined in claim 1 and L is a nucleophilically replaceable group, such as halide, $C_1$–$C_4$-alkylsulfonate, $C_1$–$C_{12}$-alkylphenylsulfonate or mono-$C_1$–$C_4$-alkyl sulfate, with an α-bisoxime of the formula III in which the substituents $R^1$ to $R^4$ are each as defined in claim 1, if appropriate in the presence of a base (see Scheme 1).

The benzyl compounds II can be prepared by syntheses known from the literature [cf. WO 95/04728 and WO 97/00866]. In the formula II, L is a nucleophilically replaceable group, for example halide, such as fluoride, chloride, bromide or iodide, in particular chloride or bromide, $C_1$–$C_4$-alkylsulfonate, such as, for example, mesylate, $C_1$–$C_{12}$-alkylphenyl sulfonate, such as, for example, tosylate, or mono-$C_1$–$C_4$-alkyl sulfate, such as, for example, methyl sulfate.

The oximes of the formula III are also known from the literature [cf. WO 97/15552] or they can be prepared by methods known from the literature [cf. WO 95/21153].

The benzyl compound II is reacted with the α-bisoxime III in a manner known per se, at from −10° C. to 100° C., preferably from 10° C. to 85° C., in an inert organic solvent in the presence of a base [cf. WO 97/02255].

Suitable solvents are ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethylformamide, dimethylacetamide and particularly preferably tetrahydrofuran, acetonitrile or dimethylformamide. It is also possible to employ mixtures of the abovementioned solvents.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, alkali metal and alkaline earth metal alkoxides, such as sodium methoxide, sodium ethoxide, potassium ethoxide, potassium tert-butoxide and dimethoxymagnesium, furthermore organic bases, for example tertiary amines, such as trimethylamine, triethylamine, diisopropylethylamine and N-methylpiperidine, pyridine, substituted pyridines, such as collidine, lutidine, and 4-dimethylaminopyridine, and also bicyclic amines. Particular preference is given to sodium hydride, potassium carbonate, sodium ethoxide and potassium tert-butoxide.

The bases are generally employed in catalytic amounts, but it is also possible to employ them in equimolar amounts, in excess or, if appropriate, as solvent.

The starting materials are generally reacted with one another in equimolar amounts. In terms of yield, it may be advantageous to employ an excess of III, based on II.

b) A further advantageous way for preparing the compounds I (see Scheme 2) starts with α-bisoxime (mono) benzyl ethers of the formula IV in which $R^1$ to $R^5$ and X are as defined in claim 1 and Y is halogen, alkylcarbonyloxy, OH, $NH_2$, $C_1$–$C_4$-alkoxy, unsubstituted or substituted phenoxy (such as, for example, p-nitrophenoxy or pentafluorophenoxy), $C_1$–$C_4$-alkylamino, di-$C_1$–$C_4$-alkylamino or an active ester, such as succinimidoxy or isourea. The compounds IV are reacted with hydroxylamine or its acid addition salt, if appropriate in the presence of a base or a dehydrating agent, such as N,N'-dicyclohexylcarbodiimide, and a compound $L^1$—W—$L^2$ in which W is as defined in claim 1 and $L^1$ and $L^2$ are each a nucleophilically replaceable group, such as halide, $C_1$–$C_4$-alkylsulfonate, $C_1$–$C_{12}$-alkylphenylsulfonate or mono-$C_1$–$C_4$-alkyl sulfate, or $L^1$ and $L^2$ together are a bridge —O—.

Scheme 2:

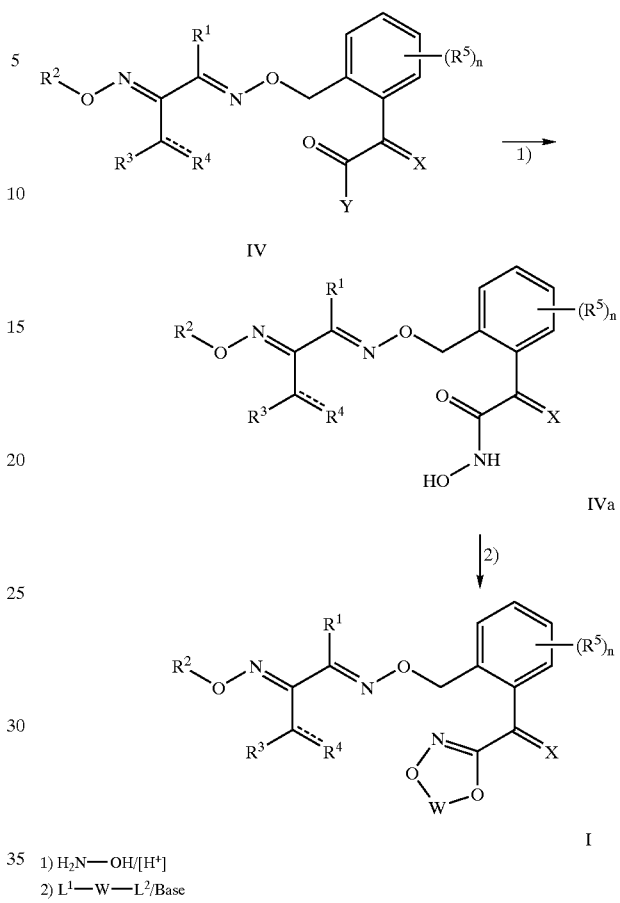

1) $H_2N$—OH/[$H^+$]
2) $L^1$—W—$L^2$/Base

The α-bisoxime (mono)benzyl ethers of the formula IV can be obtained by syntheses known from the literature [cf. WO 97/15552].

The compound $L^1$—W—$L^2$ can be prepared as described in WO 95/04728, WO 97/00866 and EP-A 846 691.

The process steps 1) and 2) shown in Scheme 2 can be carried out in two steps or, preferably, in one step, i.e. without the isolation of the hydroxamic acid IVa formed in the first process step. The reaction can be carried out similarly to the methods described in WO 95/04728, WO 97/00866 and EP-A 846 691.

The reaction mixtures are worked up in a conventional manner, for example by mixing with water, phase separation and, if required, chromatographic purification of the crude products. Some of the intermediates and end products are obtained in the form of colorless or slightly brownish viscous oils which are purified or freed from volatile components under reduced pressure and at moderately elevated temperatures. If the intermediates and end products are obtained as solids, they can also be purified by recrystallization or digestion.

Owing to their C=C— and C=N— double bonds, the compounds I can be obtained in the preparation as E/Z isomer mixtures which can be separated into the individual compounds in a customary manner, for example by crystallization or chromatography.

However, if isomer mixtures are obtained in the synthesis, a separation is generally not necessarily required since in some cases the individual isomers can be converted into each other during preparation for use or upon use (for example under the influence of light, acids, or bases). Corresponding conversions may also occur after the application, for example in the treatment of plants, in the treated plant or in the harmful fungi or animal pest to be controlled.

With regard to the —N=CR$^1$—C(CR$^3$R$^4$)=NOR$^2$ double bonds, preference is generally given to the E,E isomers of the compounds I with respect to their activity (configuration based on the radical —CH$_2$O— in relation to the —C(CR$^3$R$^4$)=NOR$^2$ group, or based on the radical —OR$^2$ in relation to the —C(R$^1$)—N=OCH$_2$-group).

In the definitions of the symbols given in the above formulae, collective terms were used which generally represent the following substituents:

halogen: fluorine, chlorine, bromine and iodine;

$C_1$–$C_4$-alkyl and the alkyl moieties of $C_1$–$C_4$-alkoxy, $C_1$–$C_4$-alkylthio, $C_1$–$C_4$-alkylamino, di-$C_1$–$C_4$-alkylamino or $C_1$–$C_4$-alkylcarbonyloxy: saturated straight-chain or branched hydrocarbon radicals having 1 to 4 carbon atoms, specifically methyl, ethyl, propyl, 1-methylethyl, butyl, 1-methylpropyl, 2-methylpropyl, 1,1-dimethylethyl;

$C_1$–$C_6$-alkyl: saturated straight-chain or branched hydrocarbon radicals having 1 to 6 carbon atoms, for example $C_1$–$C_4$-alkyl as mentioned above or pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_1$–$C_3$-alkylene: methylene, ethylene or n-propylene;

$C_1$–$C_4$-haloalkyl and the haloalkyl moieties of $C_1$–$C_4$-haloalkoxy: straight-chain or branched alkyl groups having 1 to 4 carbon atoms (as mentioned above), where the hydrogen atoms in these groups may be partly or fully replaced by halogen atoms as mentioned above, for example $C_1$–$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_3$–$C_4$-alkenyl: unsaturated straight-chain or branched hydrocarbon radicals having 3 or 4 carbon atoms and a double bond in any position, for example 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl and 2-methyl-2-propenyl;

$C_2$–$C_4$-alkenyl and the alkenyl moieties of $C_2$–$C_4$-alkenoxy: ethenyl or $C_3$–$C_4$-alkenyl (as mentioned above);

$C_2$–$C_4$-haloalkenyl and the haloalkenyl moieties of $C_2$–$C_4$-haloalkenoxy: unsaturated straight-chain or branched hydrocarbon radicals having 2 to 4 carbon atoms and a double bond in any position (as mentioned above), where the hydrogen atoms in these groups may be partly or fully replaced by halogen atoms as mentioned above, in particular by fluorine, chlorine and bromine;

$C_3$–$C_4$-alkynyl: straight-chain or branched hydrocarbon chains having 3 or 4 carbon atoms and a triple bond in any position, for example ethynyl, 1-propynyl, 2-propynyl (propargyl), 1-butynyl, 2-butynyl, 3-butynyl and 1-methyl-2-propynyl;

$C_2$–$C_4$-alkynyl and the alkynyl moieties of $C_2$–$C_4$-alkynoxy: ethynyl or $C_3$–$C_4$-alkynyl (as mentioned above);

$C_3$–$C_4$-haloalkynyl and the haloalkynyl moieties of $C_2$–$C_4$-haloalkynyloxy: unsaturated straight-chain or branched hydrocarbon radicals having 2 to 4 carbon atoms and a triple bond in any position (as mentioned above), where the hydrogen atoms in these groups may be partly or fully replaced by halogen atoms as mentioned above, in particular by fluorine, chlorine and bromine.

With regard to the phenyl radical, the term "unsubstituted or substituted" is meant to express that this radical may be partly or fully halogenated [i.e. some or all of the hydrogen atoms of this radical may be replaced by identical or different halogen atoms as mentioned above (preferably by fluorine, chlorine or bromine, in particular by fluorine or chlorine)] and/or may carry one to four (in particular one to three) of the following radicals:

halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

In particular "unsubstituted or substituted phenyl" means phenyl which is substituted by 1 to 3 halogen atoms (preferably fluorine or chlorine).

With regard to their intended use, preference is given to azadioxacycloalkenes of the formula I with the following substituents, the preference existing in each case alone or in combination:

Preference is given to compounds of the formula I in which X is $C_1$–$C_4$-alkoxy-CH= or R$^6$—CH=, where R$^6$ is halogen, $C_1$–$C_4$-alkyl, $C_1$–$C_4$-alkylthio, $C_1$–$C_4$-alkylamino or di-$C_1$–$C_4$-alkylamino and in particular CH$_3$O—CH= or CH$_3$—CH=.

Particular preference is given to compounds of the formula I in which X is $C_1$–$C_4$-alkoxy-N= and preferably CH$_3$O—N=.

Likewise, preference is given to compounds of the formula I in which n=0 or 1 and in particular 0.

Additionally, particular preference is given to compounds I in which (R$^5$)$_n$ is 6-methyl or 6-chlorine.

Equally, preference is given to compounds I in which R$^1$ is methyl, ethyl or chlorine.

Preference is furthermore given to compounds I in which R$^2$ is methyl, ethyl, n-propyl, isopropyl, n-butyl, isobutyl, s-butyl, allyl or propargyl.

Particular preference is given to compounds I in which R$^2$ is methyl or ethyl.

Moreover, preference is given to compounds I in which R$^3$ is hydrogen or methyl.

Likewise, preference is given to compounds I in which R$^4$ is =CR$^a$R$^b$, where R$^a$ and R$^b$ independently of one another are each hydrogen, methyl or ethyl. Particular preference is given to these compounds in combination with the meaning R$^3$=hydrogen.

Particular preference is given to compounds I, in which R$^4$ is =N—OR$^c$, where R$^c$ is methyl or ethyl. Particular preference is given to these compounds in combination with the meaning R$^3$=methyl.

Moreover, preference is given to compounds I in which R$^4$ is —CR$^d$=CR$^a$R$^b$ where R$^a$, R$^b$ and R$^d$ independently of one another are hydrogen, methyl or ethyl. Particular preference is given to these compounds in combination with the meaning $R^3$=hydrogen.

Furthermore, preference is given to compounds I in which W is a methyl-, ethyl- or trifluoromethyl-substituted and in particular an unsubstituted ethylene.

With a view to their use, particular preference is given to the compounds I compiled in the tables below. The groups mentioned in the tables for a substituent are furthermore on their own, independently of the combination in which they are mentioned, a particularly preferred embodiment of the substituent in question.

TABLE 1

Compounds of the formula I.A1 in which $R^1$ and $R^2$ are methyl and $R^{5*}$ is hydrogen and the combination of the radicals $R^3$, $R^a$ and $R^b$ corresponds for each compound to a row of Table A

I.A1

TABLE 2

Compounds of the formula I.A2 in which $R^1$ and $R^2$ are methyl and $R^{5*}$ is hydrogen and the combination of the radicals $R^3$, $R^a$ and $R^b$ corresponds for each compound to a row of Table A

I.A2

TABLE 3

Compounds of the formula I.A3 in which $R^1$ and $R^2$ are methyl and $R^{5*}$ is hydrogen and the combination of the radicals $R^3$, $R^a$ and $R^b$ corresponds for each compound to a row of Table A

I.A3

Table 4
Compounds of the formula I.A1 in which $R^1$ and $R^2$ are methyl and $R^{5*}$ is methyl and the combination of the radicals $R^3$, $R^a$ and $R^b$ corresponds for each compound to a row of Table A Table 5
Compounds of the formula I.A2 in which $R^1$ and $R^2$ are methyl and $R^{5*}$ is methyl and the combination of the radicals $R^3$, $R^a$ and $R^b$ corresponds for each compound to a row of Table A Table 6
Compounds of the formula I.A3 in which $R^1$ and $R^2$ are methyl and $R^{5*}$ is methyl and the combination of the radicals $R^3$, $R^a$ and $R^b$ corresponds for each compound to a row of Table A Table 7
Compounds of the formula I.A1 in which $R^1$ and $R^2$ are methyl and $R^{5*}$ is chlorine and the combination of the radicals $R^3$, $R^a$ and $R^b$ corresponds for each compound to a row of Table A Table 8
Compounds of the formula I.A2 in which $R^1$ and $R^2$ are methyl and $R^{5*}$ is chlorine and the combination of the radicals $R^3$, $R^a$ and $R^b$ corresponds for each compound to a row of Table A Table 9
Compounds of the formula I.A3 in which $R^1$ and $R^2$ are methyl and $R^{5*}$ is chlorine and the combination of the radicals $R^3$, $R^a$ and $R^b$ corresponds for each compound to a row of Table A Table 10
Compounds of the formula I.A1 in which $R^1$ is methyl, $R^2$ is ethyl and $R^{5*}$ is hydrogen and the combination of the radicals $R^3$, $R^a$ and $R^b$ corresponds for each compound to a row of Table A Table 11
Compounds of the formula I.A2 in which $R^1$ is methyl, $R^2$ is ethyl and $R^{5*}$ is hydrogen and the combination of the radicals $R^3$, $R^a$ and $R^b$ corresponds for each compound to a row of Table A Table 12
Compounds of the formula I.A3 in which $R^1$ is methyl, $R^2$ is ethyl and $R^{5*}$ is hydrogen and the combination of the radicals $R^3$, $R^a$ and $R^b$ corresponds for each compound to a row of Table A Table 13
Compounds of the formula I.A1 in which $R^1$ is methyl, $R^2$ is ethyl and $R^{5*}$ is methyl and the combination of the radicals $R^3$, $R^a$ and $R^b$ corresponds for each compound to a row of Table A Table 14
Compounds of the formula I.A2 in which $R^1$ is methyl, $R^2$ is ethyl and $R^{5*}$ is methyl and the combination of the radicals $R^3$, $R^a$ and $R^b$ corresponds for each compound to a row of Table A Table 15
Compounds of the formula I.A3 in which $R^1$ is methyl, $R^2$ is ethyl and $R^{5*}$ is methyl and the combination of the radicals $R^3$, $R^a$ and $R^b$ corresponds for each compound to a row of Table A Table 16
Compounds of the formula I.A1 in which $R^1$ is methyl, $R^2$ is ethyl and $R^{5*}$ is chlorine and the combination of the radicals $R^3$, $R^a$ and $R^b$ corresponds for each compound to a row of Table A Table 17
Compounds of the formula I.A2 in which $R^1$ is methyl, $R^2$ is ethyl and $R^{5*}$ is chlorine and the combination of the radicals $R^3$, $R^a$ and $R^b$ corresponds for each compound to a row of Table A Table 18
Compounds of the formula I.A3 in which $R^1$ is methyl, $R^2$ is ethyl and $R^{5*}$ is chlorine and the combination of the radicals $R^3$, $R^a$ and $R^b$ corresponds for each compound to a row of Table A Table 19
Compounds of the formula I.A1 in which $R^1$ is ethyl, $R^2$ is methyl and $R^{5*}$ is hydrogen and the combination of the radicals $R^3$, $R^a$ and $R^b$ corresponds for each compound to a row of Table A Table 20
Compounds of the formula I.A2 in which $R^1$ is ethyl, $R^2$ is methyl and $R^{5*}$ is hydrogen and the combination of the radicals $R^3$, $R^a$ and $R^b$ corresponds for each compound to a row of Table A Table 21
Compounds of the formula I.A3 in which $R^1$ is ethyl, $R^2$ is methyl and $R^{5*}$ is hydrogen and the combination of the radicals $R^3$, $R^a$ and $R^b$ corresponds for each compound to a row of Table A Table 22
Compounds of the formula I.A1 in which $R^1$ is ethyl, $R^2$ is methyl and $R^{5*}$ is methyl and the combination of the radicals $R^3$, $R^a$ and $R^b$ corresponds for each compound to a row of Table A Table 23
Compounds of the formula I.A2 in which $R^1$ is ethyl, $R^2$ is methyl and $R^{5*}$ is methyl and the combination of the radicals $R^3$, $R^a$ and $R^b$ corresponds for each compound to a row of Table A Table 24
Compounds of the formula I.A3 in which $R^1$ is ethyl, $R^2$ is methyl and $R^{5*}$ is methyl and the combination of the radicals $R^3$, $R^a$ and $R^b$ corresponds for each compound to a row of Table A Table 25
Compounds of the formula I.A1 in which $R^1$ is ethyl, $R^2$ is methyl and $R^{5*}$ is chlorine and the combination of the radicals $R^3$, $R^a$ and $R^b$ corresponds for each compound to a row of Table A Table 26
Compounds of the formula I.A2 in which $R^1$ is ethyl, $R^2$ is methyl and $R^{5*}$ is chlorine and the combination of the radicals $R^3$, $R^a$ and $R^b$ corresponds for each compound to a row of Table A Table 27
Compounds of the formula I.A3 in which $R^1$ is ethyl, $R^2$ is methyl and $R^{5*}$ is chlorine and the combination of the radicals $R^3$, $R^a$ and $R^b$ corresponds for each compound to a row of Table A Table 28
Compounds of the formula I.A1 in which $R^1$ and $R^2$ are ethyl and $R^{5*}$ is hydrogen and the combination of the radicals $R^3$, $R^a$ and $R^b$ corresponds for each compound to a row of Table A Table 29
Compounds of the formula I.A2 in which $R^1$ and $R^2$ are ethyl and $R^{5*}$ is hydrogen and the combination of the radicals $R^3$, $R^a$ and $R^b$ corresponds for each compound to a row of Table A Table 30
Compounds of the formula I.A3 in which $R^1$ and $R^2$ are ethyl and $R^{5*}$ is hydrogen and the combination of the radicals $R^3$, $R^a$ and $R^b$ corresponds for each compound to a row of Table A Table 31
Compounds of the formula I.A1 in which $R^1$ and $R^2$ are ethyl and $R^{5*}$ is methyl and the combination of the radicals $R^3$, $R^a$ and $R^b$ corresponds for each compound to a row of Table A Table 32
Compounds of the formula I.A2 in which $R^1$ and $R^2$ are ethyl and $R^{5*}$ is methyl and the combination of the radicals $R^3$, $R^a$ and $R^b$ corresponds for each compound to a row of Table A Table 33
Compounds of the formula I.A3 in which $R^1$ and $R^2$ are ethyl and $R^{5*}$ is methyl and the combination of the radicals $R^3$, $R^a$ and $R^b$ corresponds for each compound to a row of Table A Table 34
Compounds of the formula I.A1 in which $R^1$ and $R^2$ are ethyl and $R^{5*}$ is chlorine and the combination of the radicals $R^3$, $R^a$ and $R^b$ corresponds for each compound to a row of Table A Table 35
Compounds of the formula I.A2 in which $R^1$ and $R^2$ are ethyl and $R^{5*}$ is chlorine and the combination of the radicals $R^3$, $R^a$ and $R^b$ corresponds for each compound to a row of Table A Table 36
Compounds of the formula I.A3 in which $R^1$ and $R^2$ are ethyl and $R^{5*}$ is chlorine and the combination of the radicals $R^3$, $R^a$ and $R^b$ corresponds for each compound to a row of Table A Table 37
Compounds of the formula I.A1 in which $R^1$ is chlorine, $R^2$ is methyl and $R^{5*}$ is hydrogen and the combination of the radicals $R^3$, $R^a$ and $R^b$ corresponds for each compound to a row of Table A Table 38
Compounds of the formula I.A2 in which $R^1$ is chlorine, $R^2$ is methyl and $R^{5*}$ is hydrogen and the combination of the radicals $R^3$, $R^a$ and $R^b$ corresponds for each compound to a row of Table A Table 39
Compounds of the formula I.A3 in which $R^1$ is chlorine, $R^2$ is methyl and $R^{5*}$ is hydrogen and the combination of the radicals $R^3$, $R^a$ and $R^b$ corresponds for each compound to a row of Table A Table 40
Compounds of the formula I.A1 in which $R^1$ is chlorine, $R^2$ is methyl and $R^{5*}$ is methyl and the combination of the radicals $R^3$, $R^a$ and $R^b$ corresponds for each compound to a row of Table A Table 41
Compounds of the formula I.A2 in which $R^1$ is chlorine, $R^2$ is methyl and $R^{5*}$ is methyl and the combination of the radicals $R^3$, $R^a$ and $R^b$ corresponds for each compound to a row of Table A Table 42
Compounds of the formula I.A3 in which $R^1$ is chlorine, $R^2$ is methyl and $R^{5*}$ is methyl and the combination of the radicals $R^3$, $R^a$ and $R^b$ corresponds for each compound to a row of Table A Table 43
Compounds of the formula I.A1 in which $R^1$ is chlorine, $R^2$ is methyl and $R^{5*}$ is chlorine and the combination of the radicals $R^3$, $R^a$ and $R^b$ corresponds for each compound to a row of Table A Table 44
Compounds of the formula I.A2 in which $R^1$ is chlorine, $R^2$ is methyl and $R^{5*}$ is chlorine and the combination of the radicals $R^3$, $R^a$ and $R^b$ corresponds for each compound to a row of Table A Table 45
Compounds of the formula I.A3 in which $R^1$ is chlorine, $R^2$ is methyl and $R^{5*}$ is chlorine and the combination of the radicals $R^3$, $R^a$ and $R^b$ corresponds for each compound to a row of Table A Table 46
Compounds of the formula I.A1 in which $R^1$ is chlorine, $R^2$ is ethyl and $R^{5*}$ is hydrogen and the combination of the radicals $R^3$, $R^a$ and $R^b$ corresponds for each compound to a row of Table A Table 47
Compounds of the formula I.A2 in which $R^1$ is chlorine, $R^2$ is ethyl and $R^{5*}$ is hydrogen and the combination of the radicals $R^3$, $R^a$ and $R^b$ corresponds for each compound to a row of Table A Table 48
Compounds of the formula I.A3 in which $R^1$ is chlorine, $R^2$ is ethyl and $R^{5*}$ is hydrogen and the combination of the radicals $R^3$, $R^a$ and $R^b$ corresponds for each compound to a row of Table A Table 49
Compounds of the formula I.Al in which $R^1$ is chlorine, $R^2$ is ethyl and $R^{5*}$ is methyl and the combination of the radicals $R^3$, $R^a$ and $R^b$ corresponds for each compound to a row of Table A Table 50
Compounds of the formula I.A2 in which $R^1$ is chlorine, $R^2$ is ethyl and $R^{5*}$ is methyl and the combination of the radicals $R^3$, $R^a$ and $R^b$ corresponds for each compound to a row of Table A Table 51
Compounds of the formula I.A3 in which $R^1$ is chlorine, $R^2$ is ethyl and $R^{5*}$ is methyl and the combination of the radicals $R^3$, $R^a$ and $R^b$ corresponds for each compound to a row of Table A Table 52
Compounds of the formula I.A1 in which $R^1$ is chlorine, $R^2$ is ethyl and $R^{5*}$ is chlorine and the combination of the radicals $R^3$, $R^a$ and $R^b$ corresponds for each compound to a row of Table A Table 53
Compounds of the formula I.A2 in which $R^1$ is chlorine, $R^2$ is ethyl and $R^{5*}$ is chlorine and the combination of the radicals $R^3$, $R^a$ and $R^b$ corresponds for each compound to a row of Table A Table 54
Compounds of the formula I.A3 in which $R^1$ is chlorine, $R^2$ is ethyl and $R^{5*}$ is chlorine and the combination of the radicals $R^3$, $R^a$ and $R^b$ corresponds for each compound to a row of Table A Table 55
Compounds of the formula I.A1 in which $R^1$ is methyl, $R^2$ is n-propyl and $R^{5*}$ is hydrogen and the combination of the radicals of $R^3$, $R^a$ and $R^b$ corresponds for each compound to a row of Table A Table 56
Compounds of the formula I.A2 in which $R^1$ is methyl, $R^2$ is n-propyl and $R^{5*}$ is hydrogen and the combination of the radicals $R^3$, $R^a$ and $R^b$ corresponds for each compound to a row of Table A Table 57
Compounds of the formula I.A3 in which $R^1$ is methyl, $R^2$ is n-propyl and $R^{5*}$ is hydrogen and the combination of the radicals $R^3$, $R^a$ and $R^b$ corresponds for each compound to a row of Table A Table 58
Compounds of the formula I.A1 in which $R^1$ is methyl, $R^2$ is isopropyl and $R^{5*}$ is hydrogen and the combination of the radicals $R^3$, $R^a$ and $R^b$ corresponds for each compound to a row of Table A Table 59
Compounds of the formula I.A2 in which $R^1$ is methyl, $R^2$ is isopropyl and $R^{5*}$ is hydrogen and the combination of the radicals $R^3$, $R^a$ and $R^b$ corresponds for each compound to a row of Table A Table 60
Compounds of the formula I.A3 in which $R^1$ is methyl, $R^2$ is isopropyl and $R^{5*}$ is hydrogen and the combination of the radicals $R^3$, $R^a$ and $R^b$ corresponds for each compound to a row of Table A Table 61
Compounds of the formula I.A1 in which $R^1$ is methyl, $R^2$ is n-butyl and $R^{5*}$ is hydrogen and the combination of the radicals $R^3$, $R^a$ and $R^b$ corresponds for each compound to a row of Table A Table 62
Compounds of the formula I.A2 in which $R^1$ is methyl, $R^2$ is n-butyl and $R^{5*}$ is hydrogen and the combination of the radicals $R^3$, $R^a$ and $R^b$ corresponds for each compound to a row of Table A Table 63
Compounds of the formula I.A3 in which $R^1$ is methyl, $R^2$ is n-butyl and $R^{5*}$ is hydrogen and the combination of the radicals $R^3$, $R^a$ and $R^b$ corresponds for each compound to a row of Table A Table 64
Compounds of the formula I.A1 in which $R^1$ is methyl, $R^2$ is allyl and $R^{5*}$ is hydrogen and the combination of the radicals $R^3$, $R^a$ and $R^b$ corresponds for each compound to a row of Table A Table 65
Compounds of the formula I.A2 in which $R^1$ is methyl, $R^2$ is allyl and $R^{5*}$ is hydrogen and the combination of the radicals $R^3$, $R^a$ and $R^b$ corresponds for each compound to a row of Table A Table 66
Compounds of the formula I.A3 in which $R^1$ is methyl, $R^2$ is allyl and $R^{5*}$ is hydrogen and the combination of the radicals $R^3$, $R^a$ and $R^b$ corresponds for each compound to a row of Table A Table 67
Compounds of the formula I.A1 in which $R^1$ is methyl, $R^2$ is propargyl and $R^{5*}$ is hydrogen and the combination of the radicals $R^3$, $R^a$ and $R^b$ corresponds for each compound to a row of Table A Table 68
Compounds of the formula I.A2 in which $R^1$ is methyl, $R^2$ is propargyl and $R^{5*}$ is hydrogen and the combination of the radicals $R^3$, $R^a$ and $R^b$ corresponds for each compound to a row of Table A Table 69
Compounds of the formula I.A3 in which $R^1$ is methyl, $R^2$ is propargyl and $R^{5*}$ is hydrogen and the combination of the radicals $R^3$, $R^a$ and $R^b$ corresponds for each compound to a row of Table A

TABLE 70

Compounds of the formula I.B1 in which $R^1$ is methyl and $R^{5*}$ is hydrogen and the combination of the radicals $R^2$, $R^3$ and $R^c$ corresponds for each compound to a row of Table B

I.B1

TABLE 71

Compounds of the formula I.B2 in which $R^1$ is methyl and $R^{5*}$ is hydrogen and the combination of the radicals $R^2$, $R^3$ and $R^c$ corresponds for each compound to a row of Table B

I.B2

TABLE 72

Compounds of the formula I.B3 in which $R^1$ is methyl and $R^{5*}$ is hydrogen and the combination of the radicals $R^2$, $R^3$ and $R^c$ corresponds for each compound to a row of Table B

I.B3

Table 73
  Compounds of the formula I.B1 in which $R^1$ is methyl and $R^{5*}$ is methyl and the combination of the radicals $R^2$, $R^3$ and $R^c$ corresponds for each compound to a row of Table B
Table 74
  Compounds of the formula I.B2 in which $R^1$ is methyl and $R^{5*}$ is methyl and the combination of the radicals $R^2$, $R^3$ and $R^c$ corresponds for each compound to a row of Table B
Table 75
  Compounds of the formula I.B3 in which $R^1$ is methyl and $R^{5*}$ is methyl and the combination of the radicals $R^2$, $R^3$ and $R^c$ corresponds for each compound to a row of Table B
Table 76
  Compounds of the formula I.B1 in which $R^1$ is methyl and $R^{5*}$ is chlorine and the combination of the radicals $R^2$, $R^3$ and $R^c$ corresponds for each compound to a row of Table B
Table 77
  Compounds of the formula I.B2 in which $R^1$ is methyl and $R^{5*}$ is chlorine and the combination of the radicals $R^2$, $R^3$ and $R^c$ corresponds for each compound to a row of Table B
Table 78
  Compounds of the formula I.B3 in which $R^1$ is methyl and $R^{5*}$ is chlorine and the combination of the radicals $R^2$, $R^3$ and $R^c$ corresponds for each compound to a row of Table B
Table 79
  Compounds of the formula I.B1 in which $R^1$ is ethyl and $R^{5*}$ is hydrogen and the combination of the radicals $R^2$, $R^3$ and $R^c$ corresponds for each compound to a row of Table B
Table 80
  Compounds of the formula I.B2 in which $R^1$ is ethyl and $R^{5*}$ is hydrogen and the combination of the radicals $R^2$, $R^3$ and $R^c$ corresponds for each compound to a row of Table B
Table 81
  Compounds of the formula I.B3 in which $R^1$ is ethyl and $R^{5*}$ is hydrogen and the combination of the radicals $R^2$, $R^3$ and $R^c$ corresponds for each compound to a row of Table B
Table 82
  Compounds of the formula I.B1 in which $R^1$ is ethyl and $R^{5*}$ is methyl and the combination of the radicals $R^2$, $R^3$ and $R^c$ corresponds for each compound to a row of Table B
Table 83
  Compounds of the formula I.B2 in which $R^1$ is ethyl and $R^{5*}$ is methyl and the combination of the radicals $R^2$, $R^3$ and $R^c$ corresponds for each compound to a row of Table B
Table 84
  Compounds of the formula I.B3 in which $R^1$ is ethyl and $R^{5*}$ is methyl and the combination of the radicals $R^2$, $R^3$ and $R^c$ corresponds for each compound to a row of Table B
Table 85
  Compounds of the formula I.B1 in which $R^1$ is ethyl and $R^{5*}$ is chlorine and the combination of the radicals $R^2$, $R^3$ and $R^c$ corresponds for each compound to a row of Table B
Table 86
  Compounds of the formula I.B2 in which $R^1$ is ethyl and $R^{5*}$ is chlorine and the combination of the radicals $R^2$, $R^3$ and $R^c$ corresponds for each compound to a row of Table B
Table 87
  Compounds of the formula I.B3 in which $R^1$ is ethyl and $R^{5*}$ is chlorine and the combination of the radicals $R^2$, $R^3$ and $R^c$ corresponds for each compound to a row of Table B
Table 88
  Compounds of the formula I.B1 in which $R^1$ is chlorine and $R^{5*}$ is hydrogen and the combination of the radicals $R^2$, $R^3$ and $R^c$ corresponds for each compound to a row of Table B
Table 89
  Compounds of the formula I.B2 in which $R^1$ is chlorine and $R^{5*}$ is hydrogen and the combination of the radicals $R^2$, $R^3$ and $R^c$ corresponds for each compound to a row of Table B
Table 90
  Compounds of the formula I.B3 in which $R^1$ is chlorine and $R^{5*}$ is hydrogen and the combination of the radicals $R^2$, $R^3$ and $R^c$ corresponds for each compound to a row of Table B
Table 91
  Compounds of the formula I.B1 in which $R^1$ is chlorine and $R^{5*}$ is methyl and the combination of the radicals $R^2$, $R^3$ and $R^c$ corresponds for each compound to a row of Table B
Table 92
  Compounds of the formula I.B2 in which $R^1$ is chlorine and $R^{5*}$ is methyl and the combination of the radicals $R^2$, $R^3$ and $R^c$ corresponds for each compound to a row of Table B Table 93

Compounds of the formula I.B3 in which $R^1$ is chlorine and $R^{5*}$ is methyl and the combination of the radicals $R^2$, $R^3$ and $R^c$ corresponds for each compound to a row of Table B Table 94

Compounds of the formula I.B1 in which $R^1$ is chlorine and $R^{5*}$ is chlorine and the combination of the radicals $R^2$, $R^3$ and $R^c$ corresponds for each compound to a row of Table B Table 95

Compounds of the formula I.B2 in which $R^1$ is chlorine and $R^{5*}$ is chlorine and the combination of the radicals $R^2$, $R^3$ and $R^c$ corresponds for each compound to a row of Table B Table 96

Compounds of the formula I.B3 in which $R^1$ is chlorine and $R^{5*}$ is chlorine and the combination of the radicals $R^2$, $R^3$ and $R^c$ corresponds for each compound to a row of Table B

TABLE 97

Compounds of the formula I.C1 in which $R^1$ and $R^2$ are methyl and $R^d$ is hydrogen and the combination of the radicals $R^3$, $R^a$ and $R^b$ corresponds for each compound to a row of Table A

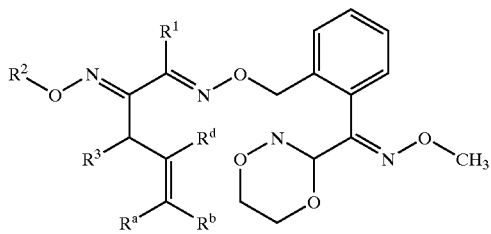

I.C1

TABLE 98

Compounds of the formula I.C2 in which $R^1$ and $R^2$ are methyl and $R^d$ is hydrogen and the combination of the radicals $R^3$, $R^a$ and $R^b$ corresponds for each compound to a row of Table A

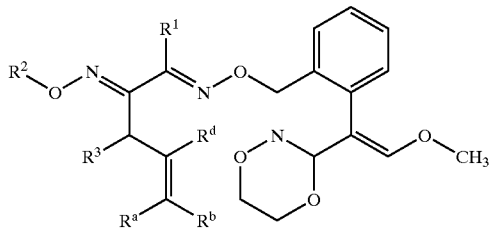

I.C2

TABLE 99

Compounds of the formula I.C3 in which $R^1$ and $R^2$ are methyl and $R^d$ is hydrogen and the combination of the radicals $R^3$, $R^a$ and $R^b$ corresponds for each compound to a row of Table A

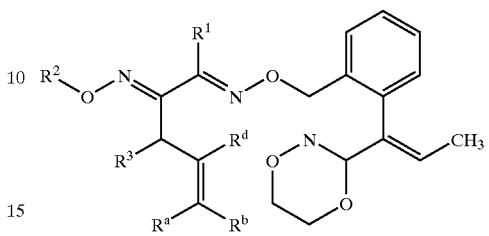

I.C3

Table 100

Compounds of the formula I.C1 in which $R^1$ and $R^2$ are methyl and $R^d$ is methyl and the combination of the radicals $R^3$, $R^a$ and $R^b$ corresponds for each compound to a row of Table A Table 101

Compounds of the formula I.C2 in which $R^1$ and $R^2$ are methyl and $R^d$ is methyl and the combination of the radicals $R^3$, $R^a$ and $R^b$ corresponds for each compound to a row of Table A Table 102

Compounds of the formula I.C3 in which $R^1$ and $R^2$ are methyl and $R^d$ is methyl and the combination of the radicals $R^3$, $R^a$ and $R^b$ corresponds for each compound to a row of Table A Table 103

Compounds of the formula I.C1 in which $R^1$ and $R^2$ are methyl and $R^d$ is ethyl and the combination of the radicals $R^3$, $R^a$ and $R^b$ corresponds for each compound to a row of Table A Table 104

Compounds of the formula I.C2 in which $R^1$ and $R^2$ are methyl and $R^d$ is ethyl and the combination of the radicals $R^3$, $R^a$ and $R^b$ corresponds for each compound to a row of Table A Table 105

Compounds of the formula I.C3 in which $R^1$ and $R^2$ are methyl and $R^d$ is ethyl and the combination of the radicals $R^3$, $R^a$ and $R^b$ corresponds for each compound to a row of Table A Table 106

Compounds of the formula I.C1 in which $R^1$ is ethyl, $R^2$ is methyl and $R^d$ is hydrogen and the combination of the radicals $R^3$, $R^a$ and $R^b$ corresponds for each compound to a row of Table A Table 107

Compounds of the formula I.C2 in which $R^1$ is ethyl, $R^2$ is methyl and $R^d$ is hydrogen and the combination of the radicals $R^3$, $R^a$ and $R^b$ corresponds for each compound to a row of Table A Table 108

Compounds of the formula I.C3 in which $R^1$ is ethyl, $R^2$ is methyl and $R^d$ is hydrogen and the combination of the radicals $R^3$, $R^a$ and $R^b$ corresponds for each compound to a row of Table A Table 109
Compounds of the formula I.C1 in which $R^1$ is ethyl, $R^2$ is methyl and $R^d$ is methyl and the combination of the radicals $R^3$, $R^a$ and $R^b$ corresponds for each compound to a row of Table A Table 110
Compounds of the formula I.C2 in which $R^1$ is ethyl, $R^2$ is methyl and $R^d$ is methyl and the combination of the radicals $R^3$, $R^a$ and $R^b$ corresponds for each compound to a row of Table A Table 111
Compounds of the formula I.C3 in which $R^1$ is ethyl, $R^2$ is methyl and $R^d$ is methyl and the combination of the radicals $R^3$, $R^a$ and $R^b$ corresponds for each compound to a row of Table A Table 112
Compounds of the formula I.C1 in which $R^1$ is ethyl, $R^2$ is methyl and $R^d$ is ethyl and the combination of the radicals $R^3$, $R^a$ and $R^b$ corresponds for each compound to a row of Table A Table 113
Compounds of the formula I.C2 in which $R^1$ is ethyl, $R^2$ is methyl and $R^d$ is ethyl and the combination of the radicals $R^3$, $R^a$ and $R^b$ corresponds for each compound to a row of Table A Table 114
Compounds of the formula I.C3 in which $R^1$ is ethyl, $R^2$ is methyl and $R^d$ is ethyl and the combination of the radicals $R^3$, $R^a$ and $R^b$ corresponds for each compound to a row of Table A Table 115
Compounds of the formula I.C1 in which $R^1$ is methyl, $R^2$ is ethyl and $R^d$ is hydrogen and the combination of the radicals $R^3$, $R^a$ and $R^b$ corresponds for each compound to a row of Table A Table 116
Compounds of the formula I.C2 in which $R^1$ is methyl, $R^2$ is ethyl and $R^d$ is hydrogen and the combination of the radicals $R^3$, $R^a$ and $R^b$ corresponds for each compound to a row of Table A Table 117
Compounds of the formula I.C3 in which $R^1$ is methyl, $R^2$ is ethyl and $R^d$ is hydrogen and the combination of the radicals $R^3$, $R^a$ and $R^b$ corresponds for each compound to a row of Table A Table 118
Compounds of the formula I.C1 in which $R^1$ is methyl, $R^2$ is ethyl and $R^d$ is methyl and the combination of the radicals $R^3$, $R^a$ and $R^b$ corresponds for each compound to a row of Table A Table 119
Compounds of the formula I.C2 in which $R^1$ is methyl, $R^2$ is ethyl and $R^d$ is methyl and the combination of the radicals $R^3$, $R^a$ and $R^b$ corresponds for each compound to a row of Table A Table 120
Compounds of the formula I.C3 in which $R^1$ is methyl, $R^2$ is ethyl and $R^d$ is methyl and the combination of the radicals $R^3$, $R^a$ and $R^b$ corresponds for each compound to a row of Table A Table 121
Compounds of the formula I.C3 in which $R^1$ is methyl, $R^2$ is ethyl and $R^d$ is ethyl and the combination of the radicals $R^3$, $R^a$ and $R^b$ corresponds for each compound to a row of Table A Table 122
Compounds of the formula I.C2 in which $R^1$ is methyl, $R^2$ is ethyl and $R^d$ is ethyl and the combination of the radicals $R^3$, $R^a$ and $R^b$ corresponds for each compound to a row of Table A Table 123
Compounds of the formula I.C3 in which $R^1$ is methyl, $R^2$ is ethyl and $R^d$ is ethyl and the combination of the radicals $R^3$, $R^a$ and $R^b$ corresponds for each compound to a row of Table A Table 124
Compounds of the formula I.C1 in which $R^1$ and $R^2$ are ethyl and $R^d$ is hydrogen and the combination of the radicals $R^3$, $R^a$ and $R^b$ corresponds for each compound to a row of Table A Table 125
Compounds of the formula I.C2 in which $R^1$ and $R^2$ are ethyl and $R^d$ is hydrogen and the combination of the radicals $R^3$, $R^a$ and $R^b$ corresponds for each compound to a row of Table A Table 126
Compounds of the formula I.C3 in which $R^1$ and $R^2$ are ethyl and $R^d$ is hydrogen and the combination of the radicals $R^3$, $R^a$ and $R^b$ corresponds for each compound to a row of Table A Table 127
Compounds of the formula I.C1 in which $R^1$ and $R^2$ are ethyl and $R^d$ is methyl and the combination of the radicals $R^3$, $R^a$ and $R^b$ corresponds for each compound to a row of Table A Table 128
Compounds of the formula I.C2 in which $R^1$ and $R^2$ are ethyl and $R^d$ is methyl and the combination of the radicals $R^3$, $R^a$ and $R^b$ corresponds for each compound to a row of Table A Table 129
Compounds of the formula I.C3 in which $R^1$ and $R^2$ are ethyl and $R^d$ is methyl and the combination of the radicals $R^3$, $R^a$ and $R^b$ corresponds for each compound to a row of Table A Table 130
Compounds of the formula I.C1 in which $R^1$ and $R^2$ are ethyl and $R^d$ is ethyl and the combination of the radicals $R^3$, $R^a$ and $R^b$ corresponds for each compound to a row of Table A Table 131
Compounds of the formula I.C2 in which $R^1$ and $R^2$ are ethyl and $R^d$ is ethyl and the combination of the radicals $R^3$, $R^a$ and $R^b$ corresponds for each compound to a row of Table A Table 132
Compounds of the formula I.C3 in which $R^1$ and $R^2$ are ethyl and $R^d$ is ethyl and the combination of the radicals $R^3$, $R^a$ and $R^b$ corresponds for each compound to a row of Table A Table 133
Compounds of the formula I.C1 in which $R^1$ is methyl, $R^2$ is n-propyl and $R^d$ is hydrogen and the combination of the radicals $R^3$, $R^a$ and $R^b$ corresponds for each compound to a row of Table A Table 134
Compounds of the formula I.C2 in which $R^1$ is methyl, $R^2$ is n-propyl and $R^d$ is hydrogen and the combination of the radicals $R^3$, $R^a$ and $R^b$ corresponds for each compound to a row of Table A Table 135
Compounds of the formula I.C3 in which $R^1$ is methyl, $R^2$ is n-propyl and $R^d$ is hydrogen and the combination of the radicals $R^3$, $R^a$ and $R^b$ corresponds for each compound to a row of Table A Table 136
Compounds of the formula I.C1 in which $R^1$ is methyl, $R^2$ is n-propyl and $R^d$ is methyl and the combination of the radicals $R^3$, $R^a$ and $R^b$ corresponds for each compound to a row of Table A Table 137
Compounds of the formula I.C2 in which $R^1$ is methyl, $R^2$ is n-propyl and $R^d$ is methyl and the combination of the radicals $R^3$, $R^a$ and $R^b$ corresponds for each compound to a row of Table A Table 138
Compounds of the formula I.C3 in which $R^1$ is methyl, $R^2$ is n-propyl and $R^d$ is methyl and the combination of the radicals $R^3$, $R^a$ and $R^b$ corresponds for each compound to a row of Table A Table 139
Compounds of the formula I.C1 in which $R^1$ is methyl, $R^2$ is n-propyl and $R^d$ is ethyl and the combination of the radicals $R^3$, $R^a$ and $R^b$ corresponds for each compound to a row of Table A Table 140
Compounds of the formula I.C2 in which $R^1$ is methyl, $R^2$ is n-propyl and $R^d$ is ethyl and the combination of the radicals $R^3$, $R^a$ and $R^b$ corresponds for each compound to a row of Table A Table 141
Compounds of the formula I.C3 in which $R^1$ is methyl, $R^2$ is n-propyl and $R^d$ is ethyl and the combination of the radicals $R^3$, $R^a$ and $R^b$ corresponds for each compound to a row of Table A Table 142
Compounds of the formula I.C1 in which $R^1$ is ethyl, $R^2$ is n-propyl and $R^d$ is hydrogen and the combination of the radicals $R^3$, $R^a$ and $R^b$ corresponds for each compound to a row of Table A Table 143
Compounds of the formula I.C2 in which $R^1$ is ethyl, $R^2$ is n-propyl and $R^d$ is hydrogen and the combination of the radicals $R^3$, $R^a$ and $R^b$ corresponds for each compound to a row of Table A Table 144
Compounds of the formula I.C3 in which $R^1$ is ethyl, $R^2$ is n-propyl and $R^d$ is hydrogen and the combination of the radicals $R^3$, $R^a$ and $R^b$ corresponds for each compound to a row of Table A Table 145
Compounds of the formula I.C1 in which $R^1$ is ethyl, $R^2$ is n-propyl and $R^d$ is methyl and the combination of the radicals $R^3$, $R^a$ and $R^b$ corresponds for each compound to a row of Table A Table 146
Compounds of the formula I.C2 in which $R^1$ is ethyl, $R^2$ is n-propyl and $R^d$ is methyl and the combination of the radicals $R^3$, $R^a$ and $R^b$ corresponds for each compound to a row of Table A Table 147
Compounds of the formula I.C3 in which $R^1$ is ethyl, $R^2$ is n-propyl and $R^d$ is methyl and the combination of the radicals $R^3$, $R^a$ and $R^b$ corresponds for each compound to a row of Table A Table 148
Compounds of the formula I.C1 in which $R^1$ is ethyl, $R^2$ is n-propyl and $R^d$ is ethyl and the combination of the radicals $R^3$, $R^a$ and $R^b$ corresponds for each compound to a row of Table A Table 149
Compounds of the formula I.C2 in which $R^1$ is ethyl, $R^2$ is n-propyl and $R^d$ is ethyl and the combination of the radicals $R^3$, $R^a$ and $R^b$ corresponds for each compound to a row of Table A Table 150
Compounds of the formula I.C3 in which $R^1$ is ethyl, $R^2$ is n-propyl and $R^d$ is ethyl and the combination of the radicals $R^3$, $R^a$ and $R^b$ corresponds for each compound to a row of Table A Table 151
Compounds of the formula I.C1 in which $R^1$ is methyl, $R^2$ is isopropyl and $R^d$ is hydrogen and the combination of the radicals $R^3$, $R^a$ and $R^b$ corresponds for each compound to a row of Table A Table 152
Compounds of the formula I.C2 in which $R^1$ is methyl, $R^2$ is isopropyl and $R^d$ is hydrogen and the combination of the radicals $R^3$, $R^a$ and $R^b$ corresponds for each compound to a row of Table A Table 153
Compounds of the formula I.C3 in which $R^1$ is methyl, $R^2$ is isopropyl and $R^d$ is hydrogen and the combination of the radicals $R^3$, $R^a$ and $R^b$ corresponds for each compound to a row of Table A Table 154
Compounds of the formula I.C1 in which $R^1$ is methyl, $R^2$ is isopropyl and $R^d$ is methyl and the combination of the radicals $R^3$, $R^a$ and $R^b$ corresponds for each compound to a row of Table A Table 155
Compounds of the formula I.C2 in which $R^1$ is methyl, $R^2$ is isopropyl and $R^d$ is methyl and the combination of the radicals $R^3$, $R^a$ and $R^b$ corresponds for each compound to a row of Table A Table 156
Compounds of the formula I.C3 in which $R^1$ is methyl, $R^2$ is isopropyl and $R^d$ is methyl and the combination of the radicals $R^3$, $R^a$ and $R^b$ corresponds for each compound to a row of Table A Table 157
Compounds of the formula I.C1 in which $R^1$ is methyl, $R^2$ is isopropyl and $R^d$ is ethyl and the combination of the radicals $R^3$, $R^a$ and $R^b$ corresponds for each compound to a row of Table A Table 158
Compounds of the formula I.C2 in which $R^1$ is methyl, $R^2$ is isopropyl and $R^d$ is ethyl and the combination of the radicals $R^3$, $R^a$ and $R^b$ corresponds for each compound to a row of Table A Table 159
Compounds of the formula I.C3 in which $R^1$ is methyl, $R^2$ is isopropyl and $R^d$ is ethyl and the combination of the radicals $R^3$, $R^a$ and $R^b$ corresponds for each compound to a row of Table A Table 160
Compounds of the formula I.C1 in which $R^1$ is ethyl, $R^2$ is isopropyl and $R^d$ is hydrogen and the combination of the radicals $R^3$, $R^a$ and $R^b$ corresponds for each compound to a row of Table A Table 161
Compounds of the formula I.C2 in which $R^1$ is ethyl, $R^2$ is isopropyl and $R^d$ is hydrogen and the combination of the radicals $R^3$, $R^a$ and $R^b$ corresponds for each compound to a row of Table A Table 162
Compounds of the formula I.C3 in which $R^1$ is ethyl, $R^2$ is isopropyl and $R^d$ is hydrogen and the combination of the radicals $R^3$, $R^a$ and $R^b$ corresponds for each compound to a row of Table A Table 163
Compounds of the formula I.C1 in which $R^1$ is ethyl, $R^2$ is isopropyl and $R^d$ is methyl and the combination of the radicals $R^3$, $R^a$ and $R^b$ corresponds for each compound to a row of Table A Table 164
Compounds of the formula I.C2 in which $R^1$ is ethyl, $R^2$ is isopropyl and $R^d$ is methyl and the combination of the radicals $R^3$, $R^a$ and $R^b$ corresponds for each compound to a row of Table A Table 165
Compounds of the formula I.C3 in which $R^1$ is ethyl, $R^2$ is isopropyl and $R^d$ is methyl and the combination of the radicals $R^3$, $R^a$ and $R^b$ corresponds for each compound to a row of Table A Table 166
Compounds of the formula I.C1 in which $R^1$ is ethyl, $R^2$ is isopropyl and $R^d$ is ethyl and the combination of the radicals $R^3$, $R^a$ and $R^b$ corresponds for each compound to a row of Table A Table 167
Compounds of the formula I.C2 in which $R^1$ is ethyl, $R^2$ is isopropyl and $R^d$ is ethyl and the combination of the radicals $R^3$, $R^a$ and $R^b$ corresponds for each compound to a row of Table A Table 168
Compounds of the formula I.C3 in which $R^1$ is ethyl, $R^2$ is isopropyl and $R^d$ is ethyl and the combination of the radicals $R^3$, $R^a$ and $R^b$ corresponds for each compound to a row of Table A Table 169
Compounds of the formula I.C1 in which $R^1$ is methyl, $R^2$ is allyl and $R^d$ is hydrogen and the combination of the radicals $R^3$, $R^a$ and $R^b$ corresponds for each compound to a row of Table A Table 170
Compounds of the formula I.C2 in which $R^1$ is methyl, $R^2$ is allyl and $R^d$ is hydrogen and the combination of the radicals $R^3$, $R^a$ and $R^b$ corresponds for each compound to a row of Table A Table 171
Compounds of the formula I.C3 in which $R^1$ is methyl, $R^2$ is allyl and $R^d$ is hydrogen and the combination of the radicals $R^3$, $R^a$ and $R^b$ corresponds for each compound to a row of Table A Table 172
Compounds of the formula I.C1 in which $R^1$ is methyl, $R^2$ is allyl and $R^d$ is methyl and the combination of the radicals $R^3$, $R^a$ and $R^b$ corresponds for each compound to a row of Table A Table 173
Compounds of the formula I.C2 in which $R^1$ is methyl, $R^2$ is allyl and $R^d$ is methyl and the combination of the radicals $R^3$, $R^a$ and $R^b$ corresponds for each compound to a row of Table A Table 174
Compounds of the formula I.C3 in which $R^1$ is methyl, $R^2$ is allyl and $R^d$ is methyl and the combination of the radicals $R^3$, $R^a$ and $R^b$ corresponds for each compound to a row of Table A Table 175
Compounds of the formula I.C1 in which $R^1$ is methyl, $R^2$ is allyl and $R^d$ is ethyl and the combination of the radicals $R^3$, $R^a$ and $R^b$ corresponds for each compound to a row of Table A Table 176
Compounds of the formula I.C2 in which $R^1$ is methyl, $R^2$ is allyl and $R^d$ is ethyl and the combination of the radicals $R^3$, $R^a$ and $R^b$ corresponds for each compound to a row of Table A Table 177
Compounds of the formula I.C3 in which $R^1$ is methyl, $R^2$ is allyl and $R^d$ is ethyl and the combination of the radicals $R^3$, $R^a$ and $R^b$ corresponds for each compound to a row of Table A Table 178
Compounds of the formula I.C1 in which $R^1$ is ethyl, $R^2$ is allyl and $R^d$ is hydrogen and the combination of the radicals $R^3$, $R^a$ and $R^b$ corresponds for each compound to a row of Table A Table 179
Compounds of the formula I.C2 in which $R^1$ is ethyl, $R^2$ is allyl and $R^d$ is hydrogen and the combination of the radicals $R^3$, $R^a$ and $R^b$ corresponds for each compound to a row of Table A Table 180
Compounds of the formula I.C3 in which $R^1$ is ethyl, $R^2$ is allyl and $R^d$ is hydrogen and the combination of the radicals $R^3$, $R^a$ and $R^b$ corresponds for each compound to a row of Table A Table 181
Compounds of the formula I.C1 in which $R^1$ is ethyl, $R^2$ is allyl and $R^d$ is methyl and the combination of the radicals $R^3$, $R^a$ and $R^b$ corresponds for each compound to a row of Table A Table 182
Compounds of the formula I.C2 in which $R^1$ is ethyl, $R^2$ is allyl and $R^d$ is methyl and the combination of the radicals $R^3$, $R^a$ and $R^b$ corresponds for each compound to a row of Table A Table 183
Compounds of the formula I.C3 in which $R^1$ is ethyl, $R^2$ is allyl and $R^d$ is methyl and the combination of the radicals $R^3$, $R^a$ and $R^b$ corresponds for each compound to a row of Table A Table 184
Compounds of the formula I.C1 in which $R^1$ is ethyl, $R^2$ is allyl and $R^d$ is ethyl and the combination of the radicals $R^3$, $R^a$ and $R^b$ corresponds for each compound to a row of Table A Table 185
Compounds of the formula I.C2 in which $R^1$ is ethyl, $R^2$ is allyl and $R^d$ is ethyl and the combination of the radicals $R^3$, $R^a$ and $R^b$ corresponds for each compound to a row of Table A Table 186
Compounds of the formula I.C3 in which $R^1$ is ethyl, $R^2$ is allyl and $R^d$ is ethyl and the combination of the radicals $R^3$, $R^a$ and $R^b$ corresponds for each compound to a row of Table A Table 187
Compounds of the formula I.C1 in which $R^1$ is methyl, $R^2$ is propargyl and $R^d$ is hydrogen and the combination of the radicals $R^3$, $R^a$ and $R^b$ corresponds for each compound to a row of Table A Table 188
Compounds of the formula I.C2 in which $R^1$ is methyl, $R^2$ is propargyl and $R^d$ is hydrogen and the combination of the radicals $R^3$, $R^a$ and $R^b$ corresponds for each compound to a row of Table A Table 189
Compounds of the formula I.C3 in which $R^1$ is methyl, $R^2$ is propargyl and $R^d$ is hydrogen and the combination of the radicals $R^3$, $R^a$ and $R^b$ corresponds for each compound to a row of Table A Table 190
Compounds of the formula I.C1 in which $R^1$ is methyl, $R^2$ is propargyl and $R^d$ is methyl and the combination of the radicals $R^3$, $R^a$ and $R^b$ corresponds for each compound to a row of Table A Table 191
Compounds of the formula I.C2 in which $R^1$ is methyl, $R^2$ is propargyl and $R^d$ is methyl and the combination of the radicals $R^3$, $R^a$ and $R^b$ corresponds for each compound to a row of Table A Table 192
Compounds of the formula I.C3 in which $R^1$ is methyl, $R^2$ is propargyl and $R^d$ is methyl and the combination of the radicals $R^3$, $R^a$ and $R^b$ corresponds for each compound to a row of Table A Table 193
Compounds of the formula I.C1 in which $R^1$ is methyl, $R^2$ is propargyl and $R^d$ is ethyl and the combination of the radicals $R^3$, $R^a$ and $R^b$ corresponds for each compound to a row of Table A Table 194
Compounds of the formula I.C2 in which $R^1$ is methyl, $R^2$ is propargyl and $R^d$ is ethyl and the combination of the radicals $R^3$, $R^a$ and $R^b$ corresponds for each compound to a row of Table A Table 195
Compounds of the formula I.C3 in which $R^1$ is methyl, $R^2$ is propargyl and $R^d$ is ethyl and the combination of the radicals $R^3$, $R^a$ and $R^b$ corresponds for each compound to a row of Table A Table 196
Compounds of the formula I.C1 in which $R^1$ is ethyl, $R^2$ is propargyl and $R^d$ is hydrogen and the combination of the radicals $R^3$, $R^a$ and $R^b$ corresponds for each compound to a row of Table A Table 197
Compounds of the formula I.C2 in which $R^1$ is ethyl, $R^2$ is propargyl and $R^d$ is hydrogen and the combination of the radicals $R^3$, $R^a$ and $R^b$ corresponds for each compound to a row of Table A Table 198
Compounds of the formula I.C3 in which $R^1$ is ethyl, $R^2$ is propargyl and $R^d$ is hydrogen and the combination of the radicals $R^3$, $R^a$ and $R^b$ corresponds for each compound to a row of Table A Table 199
Compounds of the formula I.C1 in which $R^1$ is ethyl, $R^2$ is propargyl and $R^d$ is methyl and the combination of the radicals $R^3$, $R^a$ and $R^b$ corresponds for each compound to a row of Table A Table 200
Compounds of the formula I.C2 in which $R^1$ is ethyl, $R^2$ is propargyl and $R^d$ is methyl and the combination of the radicals $R^3$, $R^a$ and $R^b$ corresponds for each compound to a row of Table A Table 201
Compounds of the formula I.C3 in which $R^1$ is ethyl, $R^2$ is propargyl and $R^d$ is methyl and the combination of the radicals $R^3$, $R^a$ and $R^b$ corresponds for each compound to a row of Table A Table 202
Compounds of the formula I.C1 in which $R^1$ is ethyl, $R^2$ is propargyl and $R^d$ is ethyl and the combination of the radicals $R^3$, $R^a$ and $R^b$ corresponds for each compound to a row of Table A Table 203
Compounds of the formula I.C2 in which $R^1$ is ethyl, $R^2$ is propargyl and $R^d$ is ethyl and the combination of the radicals $R^3$, $R^a$ and $R^b$ corresponds for each compound to a row of Table A Table 204
Compounds of the formula I.C3 in which $R^1$ is ethyl, $R^2$ is propargyl and $R^d$ is ethyl and the combination of the radicals $R^3$, $R^a$ and $R^b$ corresponds for each compound to a row of Table A

TABLE A

| No. | $R^3$ | $R^a$ | $R^b$ |
|---|---|---|---|
| A-1 | H | H | H |
| A-2 | H | H | $CH_3$ |
| A-3 | H | H | $CH_2CH_3$ |
| A-4 | H | H | $CH_2CH_2CH_3$ |
| A-5 | H | H | $CH(CH_3)_2$ |
| A-6 | H | H | $C(CH_3)_3$ |
| A-7 | H | H | $CH_2$—$C_6H_5$ |
| A-8 | H | H | CH=CH—$CH_3$ |
| A-9 | H | H | $C_6H_5$ |
| A-10 | H | H | 4-Cl—$C_6H_4$ |
| A-11 | H | H | 4-F—$C_6H_4$ |
| A-12 | H | $CH_3$ | $CH_3$ |
| A-13 | H | $CH_3$ | $CH_2CH_3$ |
| A-14 | H | $CH_3$ | $CH_2CH_2CH_3$ |
| A-15 | H | $CH_3$ | $CH(CH_3)_2$ |
| A-16 | H | $CH_3$ | $C(CH_3)_3$ |
| A-17 | H | $CH_3$ | $CH_2$—$C_6H_5$ |
| A-18 | H | $CH_3$ | $C_6H_5$ |
| A-19 | H | $CH_3$ | 4-Cl—$C_6H_4$ |
| A-20 | H | $CH_3$ | 4-F—$C_6H_4$ |
| A-21 | $CH_3$ | H | H |
| A-22 | $CH_3$ | H | $CH_3$ |
| A-23 | $CH_3$ | H | $CH_2CH_3$ |
| A-24 | $CH_3$ | H | $CH_2CH_2CH_3$ |
| A-25 | $CH_3$ | H | $CH(CH_3)_2$ |
| A-26 | $CH_3$ | H | $C(CH_3)_3$ |
| A-27 | $CH_3$ | H | $CH_2$—$C_6H_5$ |
| A-28 | $CH_3$ | H | CH=CH—$CH_3$ |
| A-29 | $CH_3$ | H | $C_6H_5$ |
| A-30 | $CH_3$ | H | 4-Cl—$C_6H_4$ |
| A-31 | $CH_3$ | H | 4-F—$C_6H_4$ |
| A-32 | $CH_3$ | $CH_3$ | H |
| A-33 | $CH_3$ | $CH_3$ | $CH_3$ |
| A-34 | $CH_3$ | $CH_3$ | $CH_2CH_3$ |
| A-35 | H | $CH_3$ | H |
| A-36 | H | $CH_2CH_3$ | H |
| A-37 | H | $CH_2CH_2CH_3$ | H |
| A-38 | H | $CH(CH_3)_2$ | H |
| A-39 | H | $C(CH_3)_3$ | H |
| A-40 | H | $CH_2$—$C_6H_5$ | H |
| A-41 | H | CH=CH—$CH_3$ | H |
| A-42 | H | $C_6H_5$ | H |
| A-43 | H | 4-Cl—$C_6H_4$ | H |
| A-44 | H | 4-F—$C_6H_4$ | H |
| A-45 | H | $CH_2CH_3$ | $CH_3$ |
| A-46 | H | $CH_2CH_2CH_3$ | $CH_3$ |
| A-47 | H | $CH(CH_3)_2$ | $CH_3$ |
| A-48 | H | $C(CH_3)_3$ | $CH_3$ |
| A-49 | H | $CH_2$—$C_6H_5$ | $CH_3$ |
| A-50 | H | $C_6H_5$ | $CH_3$ |
| A-51 | H | 4-Cl—$C_6H_4$ | $CH_3$ |
| A-52 | H | 4-F—$C_6H_4$ | $CH_3$ |
| A-53 | $CH_3$ | $CH_2CH_3$ | H |
| A-54 | $CH_3$ | $CH_2CH_2CH_3$ | H |
| A-55 | $CH_3$ | $CH(CH_3)_2$ | H |
| A-56 | $CH_3$ | $C(CH_3)_3$ | H |
| A-57 | $CH_3$ | $CH_2$—$C_6H_5$ | H |
| A-58 | $CH_3$ | CH=CH—$CH_3$ | H |
| A-59 | $CH_3$ | $C_6H_5$ | H |
| A-60 | $CH_3$ | 4-Cl—$C_6H_4$ | H |
| A-61 | $CH_3$ | 4-F—$C_6H_4$ | H |
| A-62 | $CH_3$ | $CH_2CH_3$ | $CH_3$ |
| A-63 | H | Cl | Cl |
| A-64 | H | Cl | H |
| A-65 | H | H | Cl |
| A-66 | H | Br | Br |
| A-67 | H | Br | H |
| A-68 | H | H | Br |
| A-69 | H | Cl | Br |
| A-70 | H | Br | Cl |

TABLE A-continued

| No. | R³ | Rᵃ | Rᵇ |
|---|---|---|---|
| A-71 | CH₃ | Cl | Cl |
| A-72 | CH₃ | Cl | H |
| A-73 | CH₃ | H | Cl |
| A-74 | CH₃ | Br | Br |
| A-75 | CH₃ | Br | H |
| A-76 | CH₃ | H | Br |
| A-77 | CH₃ | Cl | Br |
| A-78 | CH₃ | Br | Cl |

TABLE B

| No. | R² | R³ | Rᶜ |
|---|---|---|---|
| B-1 | CH₃ | H | CH₃ |
| B-2 | CH₃ | H | CH₂CH₃ |
| B-3 | CH₃ | H | CH₂CH₂CH₃ |
| B-4 | CH₃ | H | CH(CH₃)₂ |
| B-5 | CH₃ | H | C(CH₃)₃ |
| B-6 | CH₃ | H | CH₂CH=CH₂ |
| B-7 | CH₃ | H | CH₂C≡CH |
| B-8 | CH₃ | H | CH₂CH₂CH₂CH₃ |
| B-9 | CH₃ | CH₃ | CH₃ |
| B-10 | CH₃ | CH₃ | CH₂CH₃ |
| B-11 | CH₃ | CH₃ | CH₂CH₂CH₃ |
| B-12 | CH₃ | CH₃ | CH(CH₃)₂ |
| B-13 | CH₃ | CH₃ | C(CH₃)₃ |
| B-14 | CH₃ | CH₃ | CH₂CH=CH₂ |
| B-15 | CH₃ | CH₃ | CH₂C≡CH |
| B-16 | CH₃ | CH₃ | CH₂CH₂CH₂CH₃ |
| B-17 | CH₃ | CH₂CH₃ | CH₃ |
| B-18 | CH₃ | CH₂CH₃ | CH₂CH₃ |
| B-19 | CH₃ | CH₂CH₃ | CH₂CH₂CH₃ |
| B-20 | CH₃ | CH₂CH₃ | CH(CH₃)₂ |
| B-21 | CH₃ | CH₂CH₃ | C(CH₃)₃ |
| B-22 | CH₃ | CH₂CH₃ | CH₂CH=CH₂ |
| B-23 | CH₃ | CH₂CH₃ | CH₂C≡CH |
| B-24 | CH₃ | CH₂CH₃ | CH₂CH₂CH₂CH₃ |
| B-25 | CH₂CH₃ | H | CH₃ |
| B-26 | CH₂CH₃ | H | CH₂CH₃ |
| B-27 | CH₂CH₃ | H | CH₂CH₂CH₃ |
| B-28 | CH₂CH₃ | H | CH(CH₃)₂ |
| B-29 | CH₂CH₃ | H | C(CH₃)₃ |
| B-30 | CH₂CH₃ | H | CH₂CH=CH₂ |
| B-31 | CH₂CH₃ | H | CH₂C≡CH |
| B-32 | CH₂CH₃ | H | CH₂CH₂CH₂CH₃ |
| B-33 | CH₂CH₃ | CH₃ | CH₃ |
| B-34 | CH₂CH₃ | CH₃ | CH₂CH₃ |
| B-35 | CH₂CH₃ | CH₃ | CH₂CH₂CH₃ |
| B-36 | CH₂CH₃ | CH₃ | CH(CH₃)₂ |
| B-37 | CH₂CH₃ | CH₃ | C(CH₃)₃ |
| B-38 | CH₂CH₃ | CH₃ | CH₂CH=CH₂ |
| B-39 | CH₂CH₃ | CH₃ | CH₂C≡CH |
| B-40 | CH₂CH₃ | CH₃ | CH₂CH₂CH₂CH₃ |
| B-41 | CH₂CH₃ | CH₂CH₃ | CH₃ |
| B-42 | CH₂CH₃ | CH₂CH₃ | CH₂CH₃ |
| B-43 | CH₂CH₃ | CH₂CH₃ | CH₂CH₂CH₃ |
| B-44 | CH₂CH₃ | CH₂CH₃ | CH(CH₃)₂ |
| B-45 | CH₂CH₃ | CH₂CH₃ | C(CH₃)₃ |
| B-46 | CH₂CH₃ | CH₂CH₃ | CH₂CH=CH₂ |
| B-47 | CH₂CH₃ | CH₂CH₃ | CH₂C≡CH |
| B-48 | CH₂CH₃ | CH₂CH₃ | CH₂CH₂CH₂CH₃ |
| B-49 | (CH₂)₂CH₃ | H | CH₃ |
| B-50 | (CH₂)₂CH₃ | H | CH₂CH₃ |
| B-51 | (CH₂)₂CH₃ | H | CH₂CH₂CH₃ |
| B-52 | (CH₂)₂CH₃ | H | CH(CH₃)₂ |
| B-53 | (CH₂)₂CH₃ | H | C(CH₃)₃ |
| B-54 | (CH₂)₂CH₃ | H | CH₂CH=CH₂ |
| B-55 | (CH₂)₂CH₃ | H | CH₂C≡CH |
| B-56 | (CH₂)₂CH₃ | H | CH₂CH₂CH₂CH₃ |
| B-57 | (CH₂)₂CH₃ | CH₃ | CH₃ |
| B-48 | CH₂CH₃ | CH₂CH₃ | CH₂CH₂CH₂CH₃ |
| B-58 | (CH₂)₂CH₃ | CH₃ | CH₂CH₃ |
| B-59 | (CH₂)₂CH₃ | CH₃ | CH₂CH₂CH₃ |
| B-60 | (CH₂)₂CH₃ | CH₃ | CH(CH₃)₂ |

TABLE B-continued

| No. | R² | R³ | Rᶜ |
|---|---|---|---|
| B-61 | (CH₂)₂CH₃ | CH₃ | C(CH₃)₃ |
| B-62 | (CH₂)₂CH₃ | CH₃ | CH₂CH=CH₂ |
| B-63 | (CH₂)₂CH₃ | CH₃ | CH₂C≡CH |
| B-64 | (CH₂)₂CH₃ | CH₃ | CH₂CH₂CH₂CH₃ |
| B-65 | (CH₂)₂CH₃ | CH₂CH₃ | CH₃ |
| B-66 | (CH₂)₂CH₃ | CH₂CH₃ | CH₂CH₃ |
| B-67 | (CH₂)₂CH₃ | CH₂CH₃ | CH₂CH₂CH₃ |
| B-68 | (CH₂)₂CH₃ | CH₂CH₃ | CH(CH₃)₂ |
| B-69 | (CH₂)₂CH₃ | CH₂CH₃ | C(CH₃)₃ |
| B-70 | (CH₂)₂CH₃ | CH₂CH₃ | CH₂CH=CH₂ |
| B-71 | (CH₂)₂CH₃ | CH₂CH₃ | CH₂C≡CH |
| B-72 | (CH₂)₂CH₃ | CH₂CH₃ | CH₂CH₂CH₂CH₃ |
| B-73 | CH(CH₃)₂ | H | CH₃ |
| B-74 | CH(CH₃)₂ | H | CH₂CH₃ |
| B-75 | CH(CH₃)₂ | H | CH₂CH₂CH₃ |
| B-76 | CH(CH₃)₂ | H | CH(CH₃)₂ |
| B-77 | CH(CH₃)₂ | H | C(CH₃)₃ |
| B-78 | CH(CH₃)₂ | H | CH₂CH=CH₂ |
| B-79 | CH(CH₃)₂ | H | CH₂C≡CH |
| B-80 | CH(CH₃)₂ | H | CH₂CH₂CH₂CH₃ |
| B-81 | CH(CH₃)₂ | CH₃ | CH₃ |
| B-82 | CH(CH₃)₂ | CH₃ | CH₂CH₃ |
| B-83 | CH(CH₃)₂ | CH₃ | CH₂CH₂CH₃ |
| B-84 | CH(CH₃)₂ | CH₃ | CH(CH₃)₂ |
| B-85 | CH(CH₃)₂ | CH₃ | C(CH₃)₃ |
| B-86 | CH(CH₃)₂ | CH₃ | CH₂CH=CH₂ |
| B-87 | CH(CH₃)₂ | CH₃ | CH₂C≡CH |
| B-88 | CH(CH₃)₂ | CH₃ | CH₂CH₂CH₂CH₃ |
| B-89 | CH(CH₃)₂ | CH₂CH₃ | CH₃ |
| B-90 | CH(CH₃)₂ | CH₂CH₃ | CH₂CH₃ |
| B-91 | CH(CH₃)₂ | CH₂CH₃ | CH₂CH₂CH₃ |
| B-92 | CH(CH₃)₂ | CH₂CH₃ | CH(CH₃)₂ |
| B-93 | CH(CH₃)₂ | CH₂CH₃ | C(CH₃)₃ |
| B-94 | CH(CH₃)₂ | CH₂CH₃ | CH₂CH=CH₂ |
| B-95 | CH(CH₃)₂ | CH₂CH₃ | CH₂C≡CH |
| B-48 | CH₂CH₃ | CH₂CH₃ | CH₂CH₂CH₂CH₃ |
| B-96 | CH(CH₃)₂ | CH₂CH₃ | CH₂CH₂CH₂CH₃ |
| B-97 | (CH₂)₃CH₃ | H | CH₃ |
| B-98 | (CH₂)₃CH₃ | H | CH₂CH₃ |
| B-99 | (CH₂)₃CH₃ | H | CH₂CH₂CH₃ |
| B-100 | (CH₂)₃CH₃ | H | CH(CH₃)₂ |
| B-101 | (CH₂)₃CH₃ | H | C(CH₃)₃ |
| B-102 | (CH₂)₃CH₃ | H | CH₂CH=CH₂ |
| B-103 | (CH₂)₃CH₃ | H | CH₂C≡CH |
| B-104 | (CH₂)₃CH₃ | H | CH₂CH₂CH₂CH₃ |
| B-105 | (CH₂)₃CH₃ | CH₃ | CH₃ |
| B-106 | (CH₂)₃CH₃ | CH₃ | CH₂CH₃ |
| B-107 | (CH₂)₃CH₃ | CH₃ | CH₂CH₂CH₃ |
| B-108 | (CH₂)₃CH₃ | CH₃ | CH(CH₃)₂ |
| B-109 | (CH₂)₃CH₃ | CH₃ | C(CH₃)₃ |
| B-110 | (CH₂)₃CH₃ | CH₃ | CH₂CH=CH₂ |
| B-111 | (CH₂)₃CH₃ | CH₃ | CH₂C≡CH |
| B-112 | (CH₂)₃CH₃ | CH₃ | CH₂CH₂CH₂CH₃ |
| B-113 | (CH₂)₃CH₃ | CH₂CH₃ | CH₃ |
| B-114 | (CH₂)₃CH₃ | CH₂CH₃ | CH₂CH₃ |
| B-115 | (CH₂)₃CH₃ | CH₂CH₃ | CH₂CH₂CH₃ |
| B-116 | (CH₂)₃CH₃ | CH₂CH₃ | CH(CH₃)₂ |
| B-117 | (CH₂)₃CH₃ | CH₂CH₃ | C(CH₃)₃ |
| B-118 | (CH₂)₃CH₃ | CH₂CH₃ | CH₂CH=CH₂ |
| B-119 | (CH₂)₃CH₃ | CH₂CH₃ | CH₂C≡CH |
| B-120 | (CH₂)₃CH₃ | CH₂CH₃ | CH₂CH₂CH₂CH₃ |
| B-121 | CH₂CH(CH₃)₂ | H | CH₃ |
| B-122 | CH₂CH(CH₃)₂ | H | CH₂CH₃ |
| B-123 | CH₂CH(CH₃)₂ | H | CH₂CH₂CH₃ |
| B-124 | CH₂CH(CH₃)₂ | H | CH(CH₃)₂ |
| B-125 | CH₂CH(CH₃)₂ | H | C(CH₃)₃ |
| B-126 | CH₂CH(CH₃)₂ | H | CH₂CH=CH₂ |
| B-127 | CH₂CH(CH₃)₂ | H | CH₂C≡CH |
| B-128 | CH₂CH(CH₃)₂ | H | CH₂CH₂CH₂CH₃ |
| B-129 | CH₂CH(CH₃)₂ | CH₃ | CH₃ |
| B-130 | CH₂CH(CH₃)₂ | CH₃ | CH₂CH₃ |
| B-131 | CH₂CH(CH₃)₂ | CH₃ | CH₂CH₂CH₃ |
| B-132 | CH₂CH(CH₃)₂ | CH₃ | CH(CH₃)₂ |
| B-133 | CH₂CH(CH₃)₂ | CH₃ | C(CH₃)₃ |
| B-48 | CH₂CH₃ | CH₂CH₃ | CH₂CH₂CH₂CH₃ |
| B-134 | CH₂CH(CH₃)₂ | CH₃ | CH₂CH=CH₂ |
| B-135 | CH₂CH(CH₃)₂ | CH₃ | CH₂C≡CH |

TABLE B-continued

| No. | $R^2$ | $R^3$ | $R^c$ |
|---|---|---|---|
| B-136 | $CH_2CH(CH_3)_2$ | $CH_3$ | $CH_2CH_2CH_2CH_3$ |
| B-137 | $CH_2CH(CH_3)_2$ | $CH_2CH_3$ | $CH_3$ |
| B-138 | $CH_2CH(CH_3)_2$ | $CH_2CH_3$ | $CH_2CH_3$ |
| B-139 | $CH_2CH(CH_3)_2$ | $CH_2CH_3$ | $CH_2CH_2CH_3$ |
| B-140 | $CH_2CH(CH_3)_2$ | $CH_2CH_3$ | $CH(CH_3)_2$ |
| B-141 | $CH_2CH(CH_3)_2$ | $CH_2CH_3$ | $C(CH_3)_3$ |
| B-142 | $CH_2CH(CH_3)_2$ | $CH_2CH_3$ | $CH_2CH=CH_2$ |
| B-143 | $CH_2CH(CH_3)_2$ | $CH_2CH_3$ | $CH_2C\equiv CH$ |
| B-144 | $CH_2CH(CH_3)_2$ | $CH_2CH_3$ | $CH_2CH_2CH_2CH_3$ |
| B-145 | $CH(CH_3)CH_2CH_3$ | H | $CH_3$ |
| B-146 | $CH(CH_3)CH_2CH_3$ | H | $CH_2CH_3$ |
| B-147 | $CH(CH_3)CH_2CH_3$ | H | $CH_2CH_2CH_3$ |
| B-148 | $CH(CH_3)CH_2CH_3$ | H | $CH(CH_3)_2$ |
| B-149 | $CH(CH_3)CH_2CH_3$ | H | $C(CH_3)_3$ |
| B-150 | $CH(CH_3)CH_2CH_3$ | H | $CH_2CH=CH_2$ |
| B-151 | $CH(CH_3)CH_2CH_3$ | H | $CH_2C\equiv CH$ |
| B-152 | $CH(CH_3)CH_2CH_3$ | H | $CH_2CH_2CH_2CH_3$ |
| B-153 | $CH(CH_3)CH_2CH_3$ | $CH_3$ | $CH_3$ |
| B-154 | $CH(CH_3)CH_2CH_3$ | $CH_3$ | $CH_2CH_3$ |
| B-155 | $CH(CH_3)CH_2CH_3$ | $CH_3$ | $CH_2CH_2CH_3$ |
| B-156 | $CH(CH_3)CH_2CH_3$ | $CH_3$ | $CH(CH_3)_2$ |
| B-157 | $CH(CH_3)CH_2CH_3$ | $CH_3$ | $C(CH_3)_3$ |
| B-158 | $CH(CH_3)CH_2CH_3$ | $CH_3$ | $CH_2CH=CH_2$ |
| B-159 | $CH(CH_3)CH_2CH_3$ | $CH_3$ | $CH_2C\equiv CH$ |
| B-160 | $CH(CH_3)CH_2CH_3$ | $CH_3$ | $CH_2CH_2CH_2CH_3$ |
| B-161 | $CH(CH_3)CH_2CH_3$ | $CH_2CH_3$ | $CH_3$ |
| B-162 | $CH(CH_3)CH_2CH_3$ | $CH_2CH_3$ | $CH_2CH_3$ |
| B-163 | $CH(CH_3)CH_2CH_3$ | $CH_2CH_3$ | $CH_2CH_2CH_3$ |
| B-164 | $CH(CH_3)CH_2CH_3$ | $CH_2CH_3$ | $CH(CH_3)_2$ |
| B-165 | $CH(CH_3)CH_2CH_3$ | $CH_2CH_3$ | $C(CH_3)_3$ |
| B-166 | $CH(CH_3)CH_2CH_3$ | $CH_2CH_3$ | $CH_2CH=CH_2$ |
| B-167 | $CH(CH_3)CH_2CH_3$ | $CH_2CH_3$ | $CH_2C\equiv CH$ |
| B-168 | $CH(CH_3)CH_2CH_3$ | $CH_2CH_3$ | $CH_2CH_2CH_2CH_3$ |
| B-169 | $CH_2CH=CH_2$ | H | $CH_3$ |
| B-170 | $CH_2CH=CH_2$ | H | $CH_2CH_3$ |
| B-171 | $CH_2CH=CH_2$ | H | $CH_2CH_2CH_3$ |
| B-48 | $CH_2CH_3$ | $CH_2CH_3$ | $CH_2CH_2CH_2CH_3$ |
| B-172 | $CH_2CH=CH_2$ | H | $CH(CH_3)_2$ |
| B-173 | $CH_2CH=CH_2$ | H | $C(CH_3)_3$ |
| B-174 | $CH_2CH=CH_2$ | H | $CH_2CH=CH_2$ |
| B-175 | $CH_2CH=CH_2$ | H | $CH_2C\equiv CH$ |
| B-176 | $CH_2CH=CH_2$ | H | $CH_2CH_2CH_2CH_3$ |
| B-177 | $CH_2CH=CH_2$ | $CH_3$ | $CH_3$ |
| B-178 | $CH_2CH=CH_2$ | $CH_3$ | $CH_2CH_3$ |
| B-179 | $CH_2CH=CH_2$ | $CH_3$ | $CH_2CH_2CH_3$ |
| B-180 | $CH_2CH=CH_2$ | $CH_3$ | $CH(CH_3)_2$ |
| B-181 | $CH_2CH=CH_2$ | $CH_3$ | $C(CH_3)_3$ |
| B-182 | $CH_2CH=CH_2$ | $CH_3$ | $CH_2CH=CH_2$ |
| B-183 | $CH_2CH=CH_2$ | $CH_3$ | $CH_2C\equiv CH$ |
| B-184 | $CH_2CH=CH_2$ | $CH_3$ | $CH_2CH_2CH_2CH_3$ |
| B-185 | $CH_2CH=CH_2$ | $CH_2CH_3$ | $CH_3$ |
| B-186 | $CH_2CH=CH_2$ | $CH_2CH_3$ | $CH_2CH_3$ |
| B-187 | $CH_2CH=CH_2$ | $CH_2CH_3$ | $CH_2CH_2CH_3$ |
| B-188 | $CH_2CH=CH_2$ | $CH_2CH_3$ | $CH(CH_3)_2$ |
| B-189 | $CH_2CH=CH_2$ | $CH_2CH_3$ | $C(CH_3)_3$ |
| B-190 | $CH_2CH=CH_2$ | $CH_2CH_3$ | $CH_2CH=CH_2$ |
| B-191 | $CH_2CH=CH_2$ | $CH_2CH_3$ | $CH_2C\equiv CH$ |
| B-192 | $CH_2CH=CH_2$ | $CH_2CH_3$ | $CH_2CH_2CH_2CH_3$ |
| B-193 | $CH_2C\equiv CH$ | H | $CH_3$ |
| B-194 | $CH_2C\equiv CH$ | H | $CH_2CH_3$ |
| B-195 | $CH_2C\equiv CH$ | H | $CH_2CH_2CH_3$ |
| B-196 | $CH_2C\equiv CH$ | H | $CH(CH_3)_2$ |
| B-197 | $CH_2C\equiv CH$ | H | $C(CH_3)_3$ |
| B-198 | $CH_2C\equiv CH$ | H | $CH_2CH=CH_2$ |
| B-199 | $CH_2C\equiv CH$ | H | $CH_2C\equiv CH$ |
| B-200 | $CH_2C\equiv CH$ | H | $CH_2CH_2CH_2CH_3$ |
| B-201 | $CH_2C\equiv CH$ | $CH_3$ | $CH_3$ |
| B-202 | $CH_2C\equiv CH$ | $CH_3$ | $CH_2CH_3$ |
| B-203 | $CH_2C\equiv CH$ | $CH_3$ | $CH_2CH_2CH_3$ |
| B-204 | $CH_2C\equiv CH$ | $CH_3$ | $CH(CH_3)_2$ |
| B-205 | $CH_2C\equiv CH$ | $CH_3$ | $C(CH_3)_3$ |
| B-206 | $CH_2C\equiv CH$ | $CH_3$ | $CH_2CH=CH_2$ |
| B-207 | $CH_2C\equiv CH$ | $CH_3$ | $CH_2C\equiv CH$ |
| B-208 | $CH_2C\equiv CH$ | $CH_3$ | $CH_2CH_2CH_2CH_3$ |
| B-209 | $CH_2C\equiv CH$ | $CH_2CH_3$ | $CH_3$ |
| B-48 | $CH_2CH_3$ | $CH_2CH_3$ | $CH_2CH_2CH_2CH_3$ |
| B-210 | $CH_2C\equiv CH$ | $CH_2CH_3$ | $CH_2CH_3$ |
| B-211 | $CH_2C\equiv CH$ | $CH_2CH_3$ | $CH_2CH_2CH_3$ |
| B-212 | $CH_2C\equiv CH$ | $CH_2CH_3$ | $CH(CH_3)_2$ |
| B-213 | $CH_2C\equiv CH$ | $CH_2CH_3$ | $C(CH_3)_3$ |
| B-214 | $CH_2C\equiv CH$ | $CH_2CH_3$ | $CH_2CH=CH_2$ |
| B-215 | $CH_2C\equiv CH$ | $CH_2CH_3$ | $CH_2C\equiv CH$ |
| B-216 | $CH_2C\equiv CH$ | $CH_2CH_3$ | $CH_2CH_2CH_2CH_3$ |

The compounds I are suitable for use as fungicides. They have excellent activity against a broad spectrum of phytopathogenic fungi, in particular from the class of the Ascomycetes, Deuteromycetes, Phycomycetes and Basidiomycetes. Some of them act systemically and can be employed in crop protection as foliar- and soil-acting fungicides.

They are especially important for controlling a large number of fungi in a variety of crop plants such as wheat, rye, barley, oats, rice, maize, grass, bananas, cotton, soya, coffee, sugar cane, grapevines, fruit species, ornamentals and vegetable species such as cucumbers, beans, tomatoes, potatoes and cucurbits, and also in the seeds of these plants.

Specifically, they are suitable for controlling the following plant diseases:

Alternaria species in vegetables and fruit,

*Botrytis cinerea* (gray mold) in strawberries, vegetables, ornamentals and grapevines,

*Cercospora arachidicola* in groundnuts,

*Erysiphe cichoracearum* and *Sphaerotheca fuliginea* in cucurbits,

*Erysiphe graminis* (powdery mildew) in cereals,

Fusarium and Verticillium species in a variety of plants,

Helminthosporium species in cereals,

Mycosphaerella species in bananas and groundnuts,

*Phytophthora infestans* in potatoes and tomatoes,

*Plasmopara viticola* in grapevines,

*Podosphaera leucotricha* in apples,

*Pseudocercosporella herpotrichoides* in wheat and barley,

Pseudoperonospora species in hops and cucumbers,

Puccinia species in cereals,

*Pyricularia oryzae* in rice,

Rhizoctonia species in cotton, rice and lawns,

*Septoria nodorum* in wheat,

*Uncinula necator* in grapevines,

Ustilago species in cereals and sugar cane, and

Venturia species (scab) in apples and pears.

The compounds I are also suitable for controlling harmful fungi such as *Paecilomyces variotii* in the protection of materials (for example wood, paper, paint dispersions, fibers or tissues) and in the protection of stored products.

The compounds I are employed by treating the fungi or the plants, seeds, materials or the soil to be protected against fungal attack with a fungicidally effective amount of the active compounds. The application may be carried out before or after the infection of the materials, plants or seeds by the fungi.

The fungicidal compositions generally comprise from 0.1 to 95, preferably from 0.5 to 90,% by weight of active compound.

For use in crop protection, the application rates are, depending on the kind of effect desired, from 0.01 to 2.0 kg of active compound per ha.

The treatment of seeds generally requires active compound quantities of from 0.001 to 0.1 g, preferably from 0.01 to 0.05 g, per kilogram of seed.

For use in the protection of materials or stored products, the active compound application rate depends on the kind of application area and effect desired. Customary application rates in the protection of materials are, for example, from 0.001 g to 2 kg, preferably from 0.005 g to 1 kg, of active compound per cubic meter of treated material.

The compounds of the formula I are also suitable for the efficient control of animal pests from the classes of the insects, arachnids and nematodes. They can be used for controlling animal pests in crop protection and in the sectors of hygiene, protection of stored products and in the veterinary sector. They are particularly suitable for controlling the following animal pests:

Insects from the order of the lepidopterons (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis,* beetles (Coleoptera), e.g. *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis,* Diabrotica 12-punctata, *Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus* and *Sitophilus granaria,* dipterons (Diptera), e.g. *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa,* thrips (Thysanoptera), e.g. *Frankliniella fusca, Frankliniella occidentalis, Frankliniella tritici, Scirtothrips citri, Thrips oryzae, Thrips palmi* and *Thrips tabaci,* hymenopterons (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta,* heteropterons (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor,* homopterons (Homoptera), e.g. *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii,* termites (Isoptera), e.g. *Calotermes flavicollis, Leucotermes flavipes, Reticulitermes lucifugus* and *Termes natalensis,* orthopterons (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus,*

Arachnoidea such as arachnids (Acarina), e.g. *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora,*

*Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius* and *Tetranychus urticae,* nematodes such as root-knot nematodes, e.g. *Meloidogyne hapla, Meloidogyne incognita, Meloidogyne javanica,* cyst-forming nematodes, e.g. *Globodera rostochiensis, Heterodera avenae, Heterodera glycines, Heterodera schachtii, Heterodera trifolii,* stem and leaf nematodes, e.g. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

For controlling animal pests under outdoor conditions, the application rate of active compound is from 0.1 to 2.0, preferably 0.2 to 1.0, kg/ha.

The compounds I can be converted into the customary formulations, e.g. solutions, emulsions, suspensions, dusts, powders, pastes and granules. The use form depends on the specific intended use; in any case, it should guarantee fine and uniform distribution of the compound according to the invention.

The formulations are prepared in a known manner, e.g. by extending the active compound with solvents and/or carriers, if desired using emulsifiers and dispersants, it being possible to use other organic solvents as auxiliary solvents if water is used as the diluent. Suitable auxiliaries for this purpose are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. finely divided silica, silicates); emulsifiers such as nonionic and anionic emulsifiers (e.g. polyoxyethylene fatty alcohol ethers, alkylsulfonates and arylsulfonates), and dispersants such as ligninsulfite waste liquors and methylcellulose.

Suitable surfactants are the alkali metal, alkaline earth metal and ammonium salts of lignosulfonic acid, naphthalenesulfonic acid, phenolsulfonic acid, and dibutylnaphthalenesulfonic acid, alkylarylsulfonates, alkyl sulfates, alkylsulfonates, fatty alcohol sulfates and fatty acids and alkali metal salts and alkaline earth metal salts thereof, salts of sulfated fatty alcohol glycol ethers, condensation products of sulfonated naphthalene and naphthalene derivatives with formaldehyde, condensation products of naphthalene or of naphthalene sulfonic acid with phenol and formaldehyde, polyoxyethylene octylphenol ethers, ethoxylated isooctylphenol, octylphenol and nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Suitable for preparing directly sprayable solutions, emulsions, pastes or oil dispersions are petroleum fractions having medium to high boiling points, such as kerosene or diesel fuel, furthermore coal-tar oils and oils of plant or animal origin, aliphatic, cyclic and aromatic hydrocarbons, for example benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone, strongly polar solvents, for example dimethylformamide, dimethyl sulfoxide, N-methylpyrrolidone, and water.

Powders, compositions for broadcasting and dusts can be prepared by mixing or joint grinding of the active substances with a solid carrier.

Granules, for example coated granules, impregnated granules and homogenous granules, can be prepared by binding the active compounds to solid carriers. Solid carriers are, for example, mineral earths, such as silica gel, silicas, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of vegetable origin, such as cereal meal, tree bark meal, wood meal and nutshell meal, cellulose powders and other solid carriers.

The formulations generally comprise from 0.01 to 95% by weight, preferably from 0.1 to 90% by weight, of the active compound. The active compounds are employed in a purity of from 90% to 100%, preferably from 95% to 100% (according to the NMR spectrum). Examples of formulations are:

I. 5 parts by weight of a compound according to the invention are thoroughly mixed with 95 parts by weight of finely divided kaolin. This affords a dusting composition comprising 5% by weight of the active compound.

II. 30 parts by weight of a compound according to the invention are thoroughly mixed with a mixture of 92 parts by weight of pulverulent silica gel and 8 parts by weight of paraffin oil which had been sprayed onto the surface of this silica gel. This affords an active compound preparation having good adhesive properties (active compound content 23% by weight).

III. 10 parts by weight of a compound according to the invention are dissolved in a mixture comprising 90 parts by weight of xylene, 6 parts by weight of the addition product of 8 to 10 mol of ethylene oxide to 1 mol of oleic acid N-monoethanolamide, 2 parts by weight of the calcium salt of dodecylbenzenesulfonic acid and 2 parts by weight of the addition product of 40 mol of ethylene oxide to 1 mol of castor oil (active compound content 9% by weight).

IV. 20 parts by weight of a compound according to the invention are dissolved in a mixture comprising 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).

V. 80 parts by weight of a compound according to the invention are mixed well with 3 parts by weight of the sodium salt of diisobutylnaphthalene-α-sulfonic acid, 10 parts by weight of the sodium salt of a lignosulfonic acid from a sulfite waste liquor and 7 parts by weight of pulverulent silica gel, and ground in a hammer mill (active compound content 80% by weight).

VI. 90 parts by weight of a compound according to the invention are mixed with 10 parts by weight of N-methyl-α-pyrrolidone, affording a solution which is suitable for use in the form of very small drops (active compound content 90% by weight).

VII. 20 parts by weight of a compound according to the invention are dissolved in a mixture comprising 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. The solution is poured into 100,000 parts by weight of water and finely dispersed therein, affording an aqueous dispersion comprising 0.02% by weight of active compound.

VIII. 20 parts by weight of a compound according to the invention are mixed well with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel, and ground in a hammer mill. The mixture is finely dispersed in 20,000 parts by weight of water, affording a spray liquor comprising 0.1% by weight of active compound.

The active compounds can be applied as such, in the form of their formulations or in the application forms prepared therefrom, for example in the form of directly sprayable solutions, powders, suspensions or dispersions, emulsions, oil dispersions, pastes, dusts, compositions for broadcasting, or granules, by spraying, atomizing, dusting, broadcasting or watering. The application forms depend entirely on the intended uses; in any case, they should guarantee very fine dispersion of the active compounds according to the invention.

Aqueous use forms can be prepared from emulsion concentrates, pastes or wettable powders (spray powders, oil dispersions) by addition of water. To prepare emulsions, pastes or oil dispersions, the substances can be homogenized in water as such or dissolved in an oil or solvent, by means of wetting agents, tackifiers, dispersants or emulsifiers. However, concentrates comprising active compound, wetting agent, tackifier, dispersant or emulsifier and possibly solvent or oil which are suitable for dilution with water can also be prepared.

The active compound concentrations in the ready-to-use preparations can be varied over a relatively wide range. In general, they are from 0.0001 to 10%, preferably from 0.01 to 1%.

It is also possible to use the active compounds with a high degree of success in the ultra-low-volume method (ULV), it being possible to apply formulations comprising more than 95% by weight of active compound or even the active compound without additives.

Oils of various types, herbicides, fungicides, other pesticides and bactericides can be added to the active compounds, if desired even immediately prior to application (tank mix). These agents can be added to the compositions according to the invention in a weight ratio of 1:10 to 10:1.

The compositions according to the invention in the use form as fungicides may also be present in combination with other active compounds, for example with herbicides, insecticides, growth regulators, fungicides or else with fertilizers. In many cases, a mixture of the compounds I, or of the compositions comprising them, in the use form as fungicides with other fungicides results in a broader fungicidal spectrum of activity.

The following list of fungicides in combination with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl) disulfide;

nitro derivatives, such as dinitro-(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitro isophthalate;

heterocyclic substances, such as 2-heptadecyl-2-imidazoline acetate, 2,4-dichloro-6-(o-chloroanilino)-s-triazine, O,O-diethylphthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2))benzimidazole, 2-(thiazolyl-(4))benzimidazole, N-(1,1,2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine 2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diyl-bis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS, 3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis-(3-methoxycarbonyl-2-thioureido)benzene;

strobilurins, such as methyl E-methoximino-[α-(o-tolyloxy)-o-tolyl]acetate, methyl E-2-{2-[6-(2-cyanophenoxy)pyrimidin-4-yloxy]-phenyl}-3-methoxyacrylate, methyl E-methoximino-[α-(2- phenoxyphenyl)]acetamide, methyl-E-methoximino-[α-(2,5-dimethylphenoxy)-o-tolyl]acetamide;

anilinopyrimidines, such as N-(4,6-dimethylpyrimidin-2-yl)aniline, N-[4-methyl-6-(1-propynyl)pyrimidin-2-yl]aniline, N-(4-methyl-6-cyclopropylpyrimidin-2-yl)aniline;

phenylpyrroles, such as 4-(2,2-difluoro-1,3-benzodioxol-4-5 yl)pyrrole-3-carbonitrile;

cinnamamides, such as 3-(4-chlorophenyl)-3-(3,4-dimethoxy-phenyl)acryloylmorpholide;

and a variety of fungicides, such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzohydryl alcohol, N-(3-chloro-2,6-dinitro-4-trifluoromethylphenyl)-5-trifluoromethyl-3-chloro-2-aminopyridine, 1-((bis-(4-fluorophenyl)methylsilyl)methyl)-1H-1,2,4-triazole.

SYNTHESIS EXAMPLES

Example 1

5-methyl-hex-4-ene-2,3-dione 2-(O-(2-((5,6-dihydro-[1,4,2]-dioxazin-3-yl)methoxyiminomethyl)benzyl)oxime)3-(O-methyloxime)

Compound of I-1 of Table I)

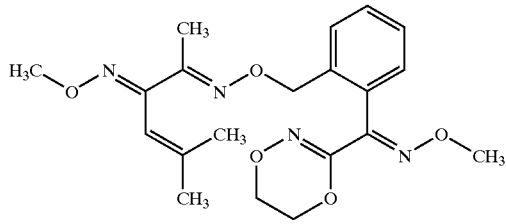

A solution of 3.3 g (59 mmol) of potassium hydroxide in 20 ml of methanol was added to a solution of 1.75 g (25 mmol) of hydroxylamine hydrochloride in 20 ml of methanol. The mixture was stirred at room temperature for 5 minutes, 4.5 g (12 mmol) of 5-methylhex-4-ene-2,3-dione 2-(O-(2-(methoxycarbonylmethoxyiminomethyl)benzyl)oxime) 3-(O-methyloxime) were then added and the mixture was stirred at 40° C. for 1 h. 1.8 g (13 mmol) of potassium carbonate and 5.1 ml (59 mmol) of 1,2-dibromoethane were subsequently added. The reaction mixture was stirred at room temperature for 18 h and then concentrated under reduced pressure, and the residue was purified by chromatography. This gave 0.6 g of the title compound as an oil.

270 MHz-$^1$H-NMR (CDCl$_3$), δ [ppm]: 1.45 (s, 3H), 1.88 (s, 3H), 2.05 (s, 3H), 3.93 (s, 3H), 3.97 (s, 3H), 4.15 (t, 2H), 4.42 (t, 2H), 5.11 (s, 2H), 5.70 (s, 1H), 7.10–7.40 (m, 4H).

The azadioxacycloalkenes listed in Tables I, II and III below can be synthesized by methods similar to the procedure given in the synthesis example above.

TABLE I

I.A1'

| No. | $R^2$ | $R^3$ | $R^a$ | $R^b$ | Phys. data |
|---|---|---|---|---|---|
| I-1 | CH$_3$ | H | CH$_3$ | CH$_3$ | IR[cm$^{-1}$]: 1447, 1369, 1093, 1046, 998. |
| I-2 | CH$_3$ | H | H | CH$_3$ | IR[cm$^{-1}$]: 1580, 1446, 1368, 1051, 998. |
| I-3 | CH$_3$ | H | H | CH$_2$CH$_3$ | IR[cm$^{-1}$]: 1580, 1462, 1368, 1050, 998. |
| I-4 | CH$_3$ | H | H | CH$_2$CH$_2$CH$_3$ | IR[cm$^{-1}$]: 1580, 1463, 1368, 1051, 998. |
| I-5 | CH$_3$ | H | H | —CH$_2$CH(CH$_3$)$_2$ | IR[cm$^{-1}$]: 1580, 1463, 1368, 1053, 998. |
| I-6 | CH$_3$ | H | Cl | Cl | $^1$H NMR, d[ppm]: 2.0(s, 3H, CH$_3$); 4.0(s, 3H, OCH$_3$); 4.2(s, 2H, CH$_2$); 4.5(s, 2H, CH$_2$); 5.1(s, 2H, CH$_2$). |
| I-7 | CH$_3$ | H | —(CH$_2$)$_4$— | | $^1$H NMR, d[ppm]: 2.1(s, 3H, CH$_3$); 4.0(s, 3H, OCH$_3$); 4.2(s, 2H, CH$_2$); 4.5(s, 2H, CH$_2$); 5.1(s, 2H, CH$_2$). |

TABLE II

I.B1'

| No. | $R^2$ | $R^3$ | $R^c$ | Phys. data |
|---|---|---|---|---|
| I-8 | CH$_3$ | CH$_3$ | CH$_3$ | m.p: 121–122° C. |
| I-9 | CH$_2$CH$_2$CH$_3$ | CH$_3$ | CH$_3$ | m.p: 99–103° C. |
| I-10 | —CH$_2$CH(CH$_3$)$_2$ | CH$_3$ | CH$_3$ | m.p: 98–102° C. |
| I-11 | CH(CH$_3$)$_2$ | CH$_3$ | CH$_3$ | $^1$H NMR, d[ppm]: 1.22(d, 6H, 2CH$_3$); 1.90 (s, 3H, CH$_3$); 2.06(s, 3H, CH$_3$); 3.91(s, 3H, OCH$_3$); 3.98 (s, 3H, OCH$_3$); 4.17(t, 3H, CH$_2$); 4.27–4.43(m, 1H, CH); 4.48(t, 3H, CH$_2$); 5.09(s, 2H, benzyl CH$_2$); 7.06–7.45(m, 4H, Ar—H). |
| I-12 | CH$_2$CH$_2$CH$_2$CH$_3$ | CH$_3$ | CH$_3$ | m.p: 49–51° C. |
| I-13 | CH$_3$ | CH$_3$ | CH$_2$C=CH | IR[cm$^{-1}$]: 2939, 1581, 1462, 1364, 1194, 1093, 1045, 1006, 906, 871 |
| I-14 | CH$_3$ | CH$_3$ | CH(CH$_3$)$_2$ | m.p: 102–105° C. |

TABLE III

I.C1'

[Structure diagram of compound I.C1' with substituents $R^2$, $R^3$, $R^a$, $R^b$, $R^d$, CH$_3$ groups, and a benzene ring with oxazine attachment]

| No. | $R^2$ | $R^3$ | $R^a$ | $R^b$ | $R^d$ | Phys. data |
|---|---|---|---|---|---|---|
| I-15 | CH$_3$ | H | H | H | CH$_3$ | IR[cm$^{-1}$]: 1447, 1369, 1046, 998. |
| I-16 | CH$_2$CH=CH$_2$ | H | H | H | CH$_3$ | IR[cm$^{-1}$]: 1580, 1447, 1369, 1046, 998. |
| I-17 | CH$_2$CH$_2$CH$_3$ | H | H | H | CH$_3$ | IR[cm$^{-1}$]: 1580, 1448, 1368, 1047, 998. |
| I-18 | CH$_2$C≡CH | H | H | H | CH$_3$ | IR[cm$^{-1}$]: 1581, 1448, 1368, 1045, 1006. |
| I-19 | CH(CH$_3$)$_2$ | H | H | H | CH$_3$ | IR[cm$^{-1}$]: 1580, 1368, 1047, 998. |

Examples of the Activity Against Harmful Fungi

The fungicidal activity of the compounds of the formula I was demonstrated by the following experiments:

The active compounds, separately or together, were formulated as a 10% strength emulsion in a mixture of 70% by weight of cyclohexanone, 20% by weight of Nekanil® LN (Lutensol® AP6, wetting agent based on ethoxylated alkylphenols having emulsifying and dispersing action) and 10% by weight of Wettol® EM (nonionic emulsifier based on ethoxylated castor oil) and diluted with water to the desired concentration.

Use Example 1

Activity Against Mildew of Wheat

Leaves of wheat seedling c.v. "Kanzler" which had been grown in pots were sprayed to runoff point with an aqueous preparation of active compound which had been prepared from a stock solution comprising 10% of active compound, 63% of cyclohexanone and 27% of emulsifier, and, 24 hours after the spray coating had dried on, dusted with spores of powdery mildew of wheat (*Erysiphe graminis* forma specialis *tritici*). The test plants were then placed in a greenhouse at 20–24° C. and 60–90% relative atmospheric humidity. After 7 days, the extent of the mildew development was determined visually in % infection of the total leaf area.

In this test, the plants which had been treated with 16 ppm of the active compounds I-1 to I-7, I-13 and I-14 showed an infection of up to 10%, whereas untreated plants were damaged to 90%.

Use Example 2

Activity Against *Plasmopara Viticola*

Leaves of potted vines c.v. "Müller-Thurgau", were sprayed to runoff point with an aqueous preparation of active compound which had been prepared from a stock solution comprising 10% of active compound, 63% of cyclohexanone and 27% of emulsifier. To be able to assess the long-term activity of the substances, the plants were kept in a greenhouse for 7 days after the spray coating had dried on. Only then were the leaves inoculated with an aqueous zoospore suspension of *Plasmopara viticola*. The vines were then first kept in a chamber saturated with water vapor at 24° C. for 48 hours, and subsequently in a greenhouse at 20–30° C. for 5 days. After this time, the plants were once more placed in a humid chamber for 16 hours to promote the eruption of sporangiophores. The extent of the fungal infection on the underside of the leaves as then determined visually.

In this test, the plants which had been treated with 63 ppm of he active compounds I-1 to I-7, I-11 to I-14 and I-16 to I-18 showed an infection of up to 15%, whereas untreated plants were damaged to 90%.

Examples of the Activity Against Animal Pests

The activity of the compounds of the formula I against animal pests was demonstrated by the following experiments:

The active compounds were formulated
a. as a 0.1% strength solution in acetone or
b. as a 10% strength emulsion in a mixture of 70% by weight of cyclohexanone, 20% by weight of % Nekanil® LN (Lutensol® AP6, wetting agent based on ethoxylated alkylphenols having emulsifying and dispersing action) and 10% by weight of Wettol® EM (nonionic emulsifier based on ethoxylated castor oil) and diluted in the case of a. with acetone and in the case of b. with water to give the desired concentration.

After the experiments had ended, in each case the lowest concentration was determined at which the compounds still caused an 80 to 100% inhibition or mortality in comparison to the untreated control experiments (limit or minimal concentration).

We claim:

1. An azadioxacycloalkene of the formula I,

I

[Structure diagram of formula I with substituents $R^1$, $R^2$, $R^3$, $R^4$, $(R^5)_n$, X, W, and heterocyclic rings]

in which the substituents $R^1$ to $R^5$ and X, the index n and the bridge member W have the following meanings:

$R^1$ is C$_1$–C$_4$-alkyl, halogen, cyano, C$_1$–C$_4$-haloalkyl or C$_3$–C$_6$-cycloalkyl;

$R^2$ is C$_1$–C$_4$-alkyl, C$_1$–C$_4$-haloalkyl, C$_3$–C$_4$-alkenyl, C$_3$–C$_4$-haloalkenyl, C$_3$–C$_4$-alkynyl or C$_3$–C$_4$-haloalkynyl;

$R^3$ is hydrogen, C$_1$–C$_4$-alkyl, C$_1$–C$_4$-haloalkyl or unsubstituted or substituted phenyl;

$R^4$ is =CR$^a$R$^b$, CR$^d$=CR$^a$R$^b$ or =N—OR$^c$, where
  R$^a$, R$^b$, R$^d$ independently of one another are each hydrogen, halogen, C$_1$–C$_6$-alkyl, C$_1$–C$_4$-haloalkyl or unsubstituted or substituted phenyl and
  R$^c$ is one of the radicals mentioned under R$^2$;

$R^5$ is nitro, cyano, halogen, C$_1$–C$_6$-alkyl or in the case that n is greater than 1, is additionally a bridge which is attached to two adjacent ring atoms and which contains three or four members selected from the group: 3 or 4 carbon atoms, 2 or 3 carbon atoms and 1 or 2 nitrogen atoms, oxygen atoms and/or sulfur atoms, where this bridge, together with the ring to which it is attached, may form a partially unsaturated or aromatic radical and where furthermore the carbon atoms of the bridge may be partly or fully substituted by halogen atoms or methyl groups;

n is 0, 1, 2, 3 or 4, where the substituents $R^5$ may be different if n is greater than 1;

X is $C_1$–$C_4$-alkoxy-N=, $C_1$–$C_4$-alkoxy-CH= or $R^6$—CH=, where $R^6$ is halogen, $C_1$–$C_4$-alkyl, $C_1$–$C_4$-alkylthio, $C_1$–$C_4$-alkylamino or di-$C_1$–$C_4$-alkylamino and W is $C_1$–$C_3$-alkylene which is unsubstituted or mono- or disubstituted by $R^7$, where $R^7$ is halogen, cyano, $C_1$–$C_4$-alkyl, $C_1$–$C_4$-haloalkyl, $C_2$–$C_4$-alkenyl, $C_2$–$C_4$-haloalkenyl, $C_2$–$C_4$-alkynyl, $C_2$–$C_4$-haloalkynyl, $C_1$–$C_4$-alkoxy, $C_1$–$C_4$-haloalkoxy, $C_2$–$C_4$-alkenoxy, $C_2$–$C_4$-haloalkenoxy, $C_2$–$C_4$-alkynoxy, $C_2$–$C_4$-haloalkynoxy or $C_1$–$C_4$-alkylcarbonyloxy.

2. An azadioxacycloalkene as claimed in claim 1, in which the substituents $R^1$ to $R^5$ and X, the index n and the bridge member W have the following meanings:

$R^1$ is methyl, ethyl or chlorine;

$R^2$ is methyl, ethyl, n-propyl, isopropyl, n-butyl, s-butyl, isobutyl, allyl or propargyl;

$R^3$ is hydrogen or methyl;

$R^4$ is =$CR^aR^b$, $CR^d$=$CR^aR^b$ or =N—$OR^c$, where $R^a$, $R^b$, $R^d$ independently of one another are each hydrogen, $C_1$–$C_4$-alkyl or phenyl, where the phenyl ring may carry from 1 to 3 substituents selected from the group: halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio and $R^c$ is one of the radicals mentioned under $R^2$;

$R^5$ is 6-methyl or 6-chlorine;

n is 0 or 1;

x is $CH_3$—O—N=, $CH_3$—O—CH= or $CH_3$—CH= and

W is unsubstituted ethylene.

3. A process for preparing compounds of the formula I as claimed in claim 1, which comprises reacting a benzyl compound of the formula II

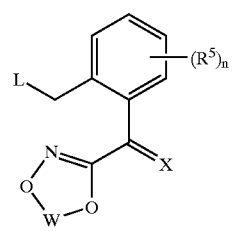

II in which the radicals $R^5$, X and W are each as defined in claim 1 and L is a nucleophilically replaceable group, with an α-bisoxime of the formula III,

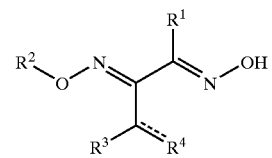

III in which the substituents $R^1$ to $R^4$ are each as defined in claim 1, if appropriate in the presence of a base.

4. A process for preparing compounds of the formula I as claimed in claim 3, wherein the nucleophilically replaceable group L is halide, $C_1$–$C_4$-alkylsulfonate, $C_1$–$C_{12}$-alkylphenylsulfonate or mono $C_1$–$C_4$-alkyl sulfate.

5. A process for preparing the compounds of the formula I as claimed in claim 1, which comprises reacting an α-bisoxime (mono)benzyl ether of the formula IV,

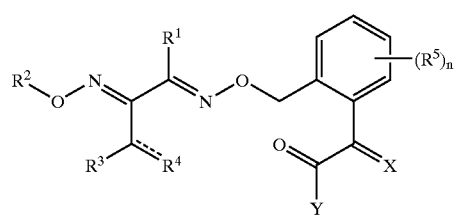

IV in which $R^1$ to $R^5$ and X are each as defined in claim 1 and Y is halogen, $C_1$–$C_4$-alkylcarbonyloxy, OH, $NH_2$, $C_1$–$C_4$-alkoxy, unsubstituted or substituted phenoxy, $C_1$–$C_4$-alkylamino, di-$C_1$–$C_4$-alkylamino or an active ester with hydroxylamine or its acid addition salt and a compound $L^1$—W—$L^2$ in which W is as defined in claim 1 and $L^1$ and $L^2$ are each a nucleophilically replaceable group, or $L^1$ and $L^2$ together are a bridge —O—, if appropriate in the presence of a base or a dehydrating agent.

6. A process for preparing compounds of the formula I as claimed in claim 5, wherein the nucleophilically replaceable groups $L^1$ and $L^2$ are each halide, $C_1$–$C_4$-alkylsulfonate, $C_1$–$C_{12}$-alkylphenylsulfonate or mono-$C_1$–$C_4$-alkyl sulfate.

7. A composition which is suitable for controlling animal pests or harmful fungi, comprising a solid or liquid carrier and a compound of the formula I as claimed in claim 1.

8. A method for controlling harmful fungi, wherein the fungi or the materials, plants, the soil or the seed to be protected against fungal attack are treated with an effective amount of a compound of the formula I as claimed in claim 1.

9. A method for controlling animal pests, wherein the animal pests or the materials, plants, the soil or the seed to be protected from them are treated with an effective amount of a compound of the formula I as claimed in claim 1.

\* \* \* \* \*